(12) United States Patent
Williams et al.

(10) Patent No.: US 12,274,876 B1
(45) Date of Patent: Apr. 15, 2025

(54) MULTIELECTRODE MEDICAL LEAD WITH FIXATION

(71) Applicants: Terrell M. Williams, Brooklyn Park, MN (US); Gopi Dandamudi, Gig Harbor, WA (US)

(72) Inventors: Terrell M. Williams, Brooklyn Park, MN (US); Gopi Dandamudi, Gig Harbor, WA (US)

(73) Assignee: The Future of Pacing L.L.C., Brooklyn Park, MN (US)

( * ) Notice: Subject to any disclaimer, the term of this patent is extended or adjusted under 35 U.S.C. 154(b) by 0 days.

(21) Appl. No.: 18/501,026

(22) Filed: Nov. 2, 2023

(51) Int. Cl.
*A61N 1/05* (2006.01)

(52) U.S. Cl.
CPC .... *A61N 1/0573* (2013.01); *A61N 2001/0578* (2013.01); *A61N 2001/058* (2013.01)

(58) Field of Classification Search
CPC .......... A61N 1/0573; A61N 2001/0578; A61N 2001/058
See application file for complete search history.

(56) References Cited

U.S. PATENT DOCUMENTS

| | | | |
|---|---|---|---|
| 4,827,940 A * | 5/1989 | Mayer | A61B 5/29 600/377 |
| 4,886,074 A * | 12/1989 | Bisping | A61N 1/0573 607/116 |
| 4,991,578 A * | 2/1991 | Cohen | A61M 25/01 607/2 |
| 5,246,014 A | 9/1993 | Williams et al. | |
| 5,306,263 A | 4/1994 | Voda | |
| 5,353,800 A * | 10/1994 | Pohndorf | A61N 1/0573 600/561 |
| 5,447,533 A * | 9/1995 | Vachon | A61N 1/056 600/374 |
| 5,476,497 A | 12/1995 | Mower et al. | |
| 5,522,876 A * | 6/1996 | Rusink | A61N 1/0573 607/128 |
| 5,531,783 A * | 7/1996 | Giele | A61N 1/0573 600/375 |
| 5,617,854 A | 4/1997 | Munsif | |
| 5,658,326 A * | 8/1997 | Barsne | A61N 1/0573 607/126 |
| 5,772,693 A | 6/1998 | Brownlee | |
| 5,851,226 A | 12/1998 | Skubitz et al. | |

(Continued)

OTHER PUBLICATIONS

Abdelrahman et al., Clinical Outcomes of His Bundle Pacing Compared to Right Ventricular Pacing, JACC vol. 71, No. 20, May 22, 2018, pp. 2319-2330, The American College of Cardiology Foundation, Washington, DC.

(Continued)

*Primary Examiner* — Eric D. Bertram
(74) *Attorney, Agent, or Firm* — Lund IP, PLLC

(57) ABSTRACT

A medical lead includes a lead body, a lead body helix extending from a distal end of the lead body, wherein the lead body helix is configured to anchor to a patient tissue, and, a cable within the lead body, the cable including a cable conductor, a cable electrode proximate a distal end of the cable conductor, and a cable helix with a blunt tip at a distal end of the cable. The cable is slidable within the lead body to extend and retract the cable electrode along a trajectory extending from the distal end of the lead body.

29 Claims, 11 Drawing Sheets

(56) References Cited

U.S. PATENT DOCUMENTS

| | | | |
|---|---|---|---|
| 5,876,385 A | 3/1999 | Ikari et al. | |
| 5,964,795 A * | 10/1999 | McVenes | A61N 1/056 607/122 |
| 5,987,746 A | 11/1999 | Williams | |
| 6,004,280 A | 12/1999 | Buck et al. | |
| 6,066,126 A | 5/2000 | Li et al. | |
| 6,091,978 A * | 7/2000 | Johnson | A61N 1/0568 600/375 |
| 6,214,016 B1 | 4/2001 | Williams et al. | |
| 6,366,819 B1 | 4/2002 | Stokes | |
| 6,408,214 B1 * | 6/2002 | Williams | A61M 25/0041 607/122 |
| 6,419,868 B1 * | 7/2002 | Johnson | A61N 1/0573 264/249 |
| 6,931,286 B2 * | 8/2005 | Sigg | A61M 25/0084 607/126 |
| 6,937,897 B2 | 8/2005 | Min et al. | |
| 6,988,007 B1 * | 1/2006 | Morgan | A61N 1/056 600/374 |
| 7,044,934 B2 * | 5/2006 | Mickley | A61M 25/0041 604/164.01 |
| 7,056,294 B2 | 6/2006 | Khairkhahan et al. | |
| 7,082,335 B2 * | 7/2006 | Klein | A61N 1/056 607/126 |
| 7,177,704 B2 | 2/2007 | Laske et al. | |
| 7,191,015 B2 * | 3/2007 | Lamson | A61N 1/056 607/129 |
| 7,386,351 B2 * | 6/2008 | Hine | A61N 1/056 607/122 |
| 7,496,410 B2 * | 2/2009 | Heil, Jr. | A61N 1/059 607/126 |
| 7,647,124 B2 | 1/2010 | Williams | |
| 7,657,325 B2 | 2/2010 | Williams | |
| 7,729,782 B2 | 6/2010 | Williams et al. | |
| 8,100,883 B1 | 1/2012 | Johnson | |
| 8,332,042 B2 | 12/2012 | Williams | |
| 8,406,899 B2 | 3/2013 | Reddy et al. | |
| 8,606,369 B2 | 12/2013 | Williams et al. | |
| 8,620,433 B2 | 12/2013 | Ghosh et al. | |
| 8,670,824 B2 | 3/2014 | Anderson et al. | |
| 8,744,579 B2 | 6/2014 | Parikh et al. | |
| 9,504,801 B2 | 11/2016 | Dangoisse | |
| 9,579,501 B2 | 2/2017 | Shuros et al. | |
| 9,662,501 B2 | 5/2017 | Mongeon et al. | |
| 9,700,729 B2 | 7/2017 | Ghosh et al. | |
| 10,737,097 B2 | 8/2020 | Williams et al. | |
| 10,773,087 B1 | 9/2020 | Williams et al. | |
| RE48,319 E | 11/2020 | Sambelashvili | |
| 10,888,354 B2 | 1/2021 | Kugler et al. | |
| 11,253,699 B1 * | 2/2022 | Williams | A61N 1/0573 |
| 11,446,486 B1 * | 9/2022 | Dandamudi | A61N 1/0573 |
| 11,583,658 B2 | 2/2023 | Yang et al. | |
| 11,654,278 B1 | 5/2023 | Williams et al. | |
| 2002/0165442 A1 * | 11/2002 | Heil, Jr. | A61N 1/0573 600/375 |
| 2003/0023296 A1 * | 1/2003 | Osypka | A61N 1/056 607/122 |
| 2003/0130713 A1 | 7/2003 | Stewart et al. | |
| 2003/0204233 A1 | 10/2003 | Laske et al. | |
| 2004/0064158 A1 * | 4/2004 | Klein | A61N 1/056 607/9 |
| 2006/0206153 A1 * | 9/2006 | Libbus | A61N 1/3627 607/9 |
| 2008/0228171 A1 | 9/2008 | Kugler et al. | |
| 2009/0105724 A1 | 4/2009 | Yoshizaki et al. | |
| 2010/0069983 A1 | 3/2010 | Peacock, III et al. | |
| 2010/0179630 A1 | 7/2010 | Williams | |
| 2010/0305670 A1 * | 12/2010 | Hall | A61N 1/3752 29/879 |
| 2012/0004714 A1 * | 1/2012 | Kleve | A61N 1/0563 607/116 |
| 2014/0046389 A1 * | 2/2014 | Anderson | A61N 1/3684 607/4 |
| 2014/0067036 A1 * | 3/2014 | Shuros | A61N 1/0573 606/129 |
| 2018/0078772 A1 | 3/2018 | Williams et al. | |
| 2019/0022379 A1 * | 1/2019 | Foster | A61N 1/0573 |
| 2019/0321625 A1 * | 10/2019 | Shuros | A61N 1/0573 |
| 2020/0114146 A1 * | 4/2020 | Foster | A61N 1/0565 |
| 2020/0155798 A1 | 5/2020 | Yang et al. | |
| 2020/0261734 A1 * | 8/2020 | Yang | A61N 1/0573 |

OTHER PUBLICATIONS

Kawashima et al., A macroscopic anatomical investigation of atrioventricular bundle locational variation relative to the membranous part of the ventricular septum in elderly human hearts, Surgical & Radiologic Anatomy, Feb. 19, 2005, pp. 206-213, vol. 27, Springer-Verlag, Heidelberg, Germany.

Kawashima et al., In situ anatomy map provides a new scenario for conduction system pacing, European Heart Journal, Jul. 21, 2023, pp. 2508-2510, vol. 44, Issue 28, Oxford, England.

Medtronic, 6416: Temporary transvenous pacing lead system, Jul. 7, 2015, Medtronic, Inc., Minneapolis, Minnesota.

Medtronic, C315 Catheter: For the SelectSecure® Pacing lead system, Dec. 2008, Medtronic, Inc., Minneapolis, Minnesota.

Medtronic, His-Bundle Pacing Introductory Tutorial, May 2017, Medtronic, Inc., Minneapolis, Minnesota.

Medtronic, The SelectSite® Catheter: Giving You Control Where to Place the Lead, Mar. 2007, Medtronic, Inc., Minneapolis, Minnesota.

Nakazato, Safety and usefulness of the Sweet Tip™ type screw-in lead for pacemakers, Journal of Arrhythmia, Apr. 22, 2014, pp. 88-91, vol. 30, Issue 2, Tokyo, Japan.

Vijayaraman et al., Prospective evaluation of feasibility and electrophysiologic and echocardiographic characteristics of left bundle branch area pacing, Heart Rhythm vol. 16, No. 12, Dec. 2019, pp. 1774-1782, Heart Rhythm Society, Washington, DC.

* cited by examiner

MULTIELECTRODE MEDICAL LEAD WITH FIXATION

TECHNICAL FIELD

This disclosure relates to cardiac pacing.

BACKGROUND

Typically, pacing leads are deployed to various locations in the heart depending on the nature of the heart condition necessitating the pacing procedure. Conventional ventricular pacing typically involves implanting a lead at the apex of the right ventricle. This placement is still often utilized today even in the face of published evidence of the deleterious effects of bypassing the His/Purkinje system, otherwise known as the cardiac conduction system.

Pacemaker lead electrodes have been regularly placed in or on the heart in a position that bypasses the His/Purkinje system since the inception of pacing in 1957. Conventional pacing directly stimulates the myocardium and has been the standard of care even though His bundle pacing has been known and tried occasionally.

During and around the 1980s, scientific studies found that over time, ventricular pacing resulted in what was termed, "ventricular remodeling," which can result in a number of detrimental effects including: myofiber disarray, fatty tissue and fibrotic deposits away from the electrode, impaired endothelium function, acute hemodynamic compromise, redistribution of myocardial fiber strain and blood flow, with hypertrophy away from the electrode, mitral valve regurgitation due to poor papillary muscle timing, cardiac sympathetic activity, decreases in left ventricle (LV) chamber efficiency, slowing of LV isovolumic relaxation, far LV wall contracting against a closed aortic valve, tricuspid valve insufficiency due to lead mechanical disruption, and mitochondrial abnormality away from the electrode.

By 2002, large, controlled studies found that conventional ventricular pacing also resulted in heart failure hospitalization and mortality, especially when the patient was paced forty percent or more or the time. This iatrogenic problem is referred to as "pacing induced heart failure."

In spite of significant research demonstrating significant mortality reductions for His bundle pacing compared to conventional pacing, the value of His pacing has not been widely recognized or practiced among clinicians responsible for implanting cardiac pacing leads and pacemakers.

BRIEF SUMMARY

The inventors believe the limited prevalence of His bundle pacing, and when required, pacing the left bundle branch (LBB) of the conduction system, is in part due to lack of effective leads and lead delivery systems. The His bundle consists of two discreet bundles which separate at the crest of the ventricular septum to form the LBB and right bundle branch (RBB). The cardiac conduction system is comprised in part of His bundle which resides between the atrioventricular (AV) node, and the bifurcation of the LBB and RBB. These anatomic locations are regarded as difficult targets to reach.

For example, many patients cannot have LBB block corrected by His bundle pacing but can benefit from LBB pacing. Techniques disclosed herein facilitate both His bundle pacing, generally via the septal wall of the right atrium, and LBB pacing, generally via right ventricle (RV) septal access. The present disclosure describes examples of leads and methods for use including delivering a pacing lead to the LBB, at the septal wall of the RV or the His bundle in the right atrium.

Examples of the present disclosure includes a coaxial lead including a lead body with a distal lead body helix to facilitate anchoring to the septal wall of the RV proximate the RBB or, alternatively, proximate the His bundle, generally via the septal wall of the right atrium. Such leads may further include central cable with a blunt cable helix configured for deployment within the septum. The central cable includes a cable electrode that may be advanced to the His bundle or LBB following anchoring the distal end of the lead body into the septal wall with the lead body helix. The blunt cable helix facilitates blunt dissection of the septal wall during cable advancement while mitigating risk of perforation of the septum into the LV. Once a target site is reached, the central cable is turned to anchor the blunt cable helix at the target site.

The lead may be implanted via a catheter. Implantation techniques may include selecting a trajectory for the blunt cable helix by manipulating the catheter after anchoring the cable helix to the septal wall. For example, with the distal end of the catheter-lead assembly anchored to the septal wall, the direction of the trajectory of the blunt cable helix may be selected by the clinician by bending the catheter through pushing and pulling from a proximal location outside the body of the patient to blunt dissect tissue with the cable helix, as well by rotating the catheter from the outside the body of the patient to anchor the cable helix.

In one example, this disclosure is directed to a medical lead including a lead body, a lead body helix extending from a distal end of the lead body, wherein the lead body helix is configured to anchor to a patient tissue, and, a cable within the lead body, the cable including a cable conductor, a cable electrode proximate a distal end of the cable conductor, and a cable helix with a blunt tip at a distal end of the cable. The cable is slidable within the lead body to extend and retract the cable electrode along a trajectory extending from the distal end of the lead body.

In another example, this disclosure is directed to a method for implanting a medical lead the medical lead including, a lead body, a lead body helix extending from a distal end of the lead body, wherein the lead body helix is configured to anchor to a patient tissue, and a cable within the lead body, the cable including a cable conductor, a cable electrode proximate a distal end of the cable conductor, and a cable helix with a blunt tip at a distal end of the cable. The cable is slidable within the lead body to extend and retract the cable electrode along a trajectory extending from the distal end of the lead body. The method includes securing the lead body helix of to a patient tissue proximate a target site, extending the cable conductor from the lead body to blunt dissect the patient tissue with the cable helix, and rotating the cable conductor relative to the lead body to anchor the cable helix to the patient tissue.

DETAILED DESCRIPTION

Figure 1:
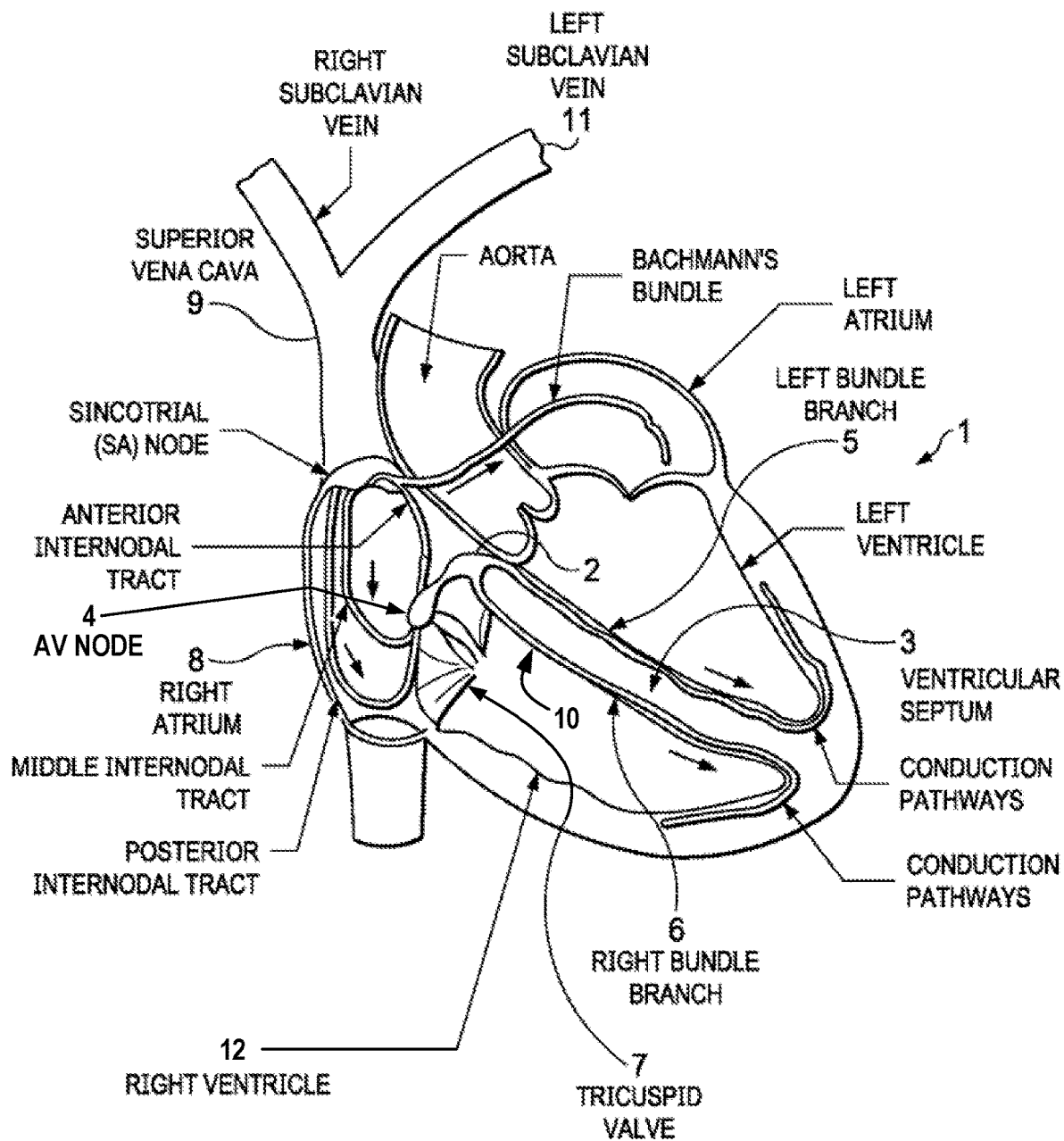
FIG. 1 is a cross-sectional illustration of a human heart depicting the anatomy of the heart and its electrical system.

The prevalence of His bundle pacing or LBB pacing, though increasing, is practiced in a small minority of pacing lead implantations both in the United States and worldwide. The His bundle and LBB present a small targets and are hard to reach successfully. This increases fluoroscopy or "flouro" time, which is a detriment to both patient and the surgical clinician. However, in one study by the inventors, the mortality rate of one hospital doing conventional pacing was compared with the mortality rate with another hospital doing pacing at the His bundle (for normal physiological ventricular activation). Heart failure and patient mortality was lower at the hospital providing physiological ventricular activation by His bundle pacing.

It is generally more difficult to place a cardiac lead electrode at the conduction system for His bundle pacing or LBB pacing than it is to place within the RV for conventional pacing. However, techniques of the present disclosure mitigate difficulties with locating a lead electrode to capture the His bundle or LBB. Locating a lead electrode to capture the LBB, which is important for patients with LBB block in which the capturing the His bundle may not provide effective LBB normalization. Disclosed techniques also facilitate capturing the RBB, e.g., for bifocal stimulation and/or to facilitate cardiac resynchronization.

In one example, a lead includes an anode ring electrode, and a helical electrode anchor configured to be anchored on the septum of the right atrium, piercing the endocardial membrane of the right atrium. The helical electrode may capture the RBB. A blunt cable helix is connected via a cable conductor extending from the connector end of the lead. A clinician advances the cable conductor through the coaxial center of the lead, advancing the blunt cable helix via the pierced endocardial membrane of the RV to a targeted portion of the cardiac conduction system, usually the His bundle within the septum or extending distally to the LBB.

The trajectory of the blunt cable helix is controlled by the angle of the lead delivery catheter following anchoring of the helical electrode anchor. While anchored, the clinician may manipulate the angle of lead delivery catheter. The catheter pivots the helical electrode, controlling the trajectory of the blunt cable helix.

In this manner, the catheter and fixation screw need not be presented at any particular angle (such as perpendicular) to the endocardial surface. The trajectory of the blunt cable helix can be manipulated after helical electrode fixation and has no bearing on His pacing threshold. Thus, a variety of lead delivery catheters may be suitable for delivery of leads disclosed herein.

Once the clinician is satisfied with the angle of the catheter, the clinician advances the cable, having the blunt cable helix attached at the distal tip, is advanced from the connector end, through the lead body and helical electrode to the targeted portion of the cardiac conduction system, e.g., via blunt dissection. In other examples, the tissue may be cut with a sharp electrode or RF energy. However, blunt dissection may provide an advantage of mitigating the risk of piercing the septum as the endocardial membrane of the ventricular septum provides a relatively durable and elastic layer resistant to blunt dissection compared to the muscular central portion of the ventricular septum.

Selection of either specific or nonspecific His bundle pacing can be achieved for type two His anatomy because of the blunt cable helix is small enough to fit within the His bundle. Type two His anatomy, existing in an estimated 32% of patients, is where the His bundle dives below the central fibrous body and is surrounded by myocardium. Large electrodes, such as helical electrodes of current leads may be too large to exclude the myocardium from activation along with the His bundle (called non-specific His bundle pacing). In contrast, smaller electrodes of leads disclosed herein, such as those with an electrode radius of about 0.5 millimeters (mm), allow for "specific" His bundle pacing. Such smaller electrodes may also facilitate LBB pacing, in the event that LBB block cannot be corrected at the His bundle due to infra-hisian block, e.g., through trans-septal lead placement.

In contrast, a clinician attempting to use a conventional screw-in lead meant for RV or atrial endocardial attachment may try to drill thru the septum-a process that is very tedious, reportedly requiring at times, forty turns, and having the risk of penetration into the lumen of the LV risking embolic stroke.

In examples where the helical electrode anchor includes a helical electrode, which facilitates targeting the RBB, either simultaneously or independently of the LBB, e.g., for cardiac resynchronization. The multiple electrode configuration of leads disclosed herein provide a number of options for stimulation of the His bundle, RBB and/or LBB. Moreover, stimulation parameters may be reprogrammed without further surgical intervention if needed to overcome post-implantation degradation of the hearts conduction system.

FIG. 1 shows the cardiac anatomy, especially the cardiac conduction system. In a healthy heart, the natural pacemaker, the SA node, activates the high conduction velocity Purkinje fibers within the right and left atria, resulting in coordinated atrial muscle cell contraction. This injects blood collected in the atria, into the powerful left and right ventricles. There is a pause in conduction at the AV node allowing the ventricles to fill. Then, just before blood flows back into the atria, the AV node activates the His bundle and, by high conduction velocity, the left and right bundle branches and the entire Purkinje system. This choreographs ventricular contraction, endocardial myocardium contracting first followed by epicardial muscle contraction. This programmed ventricular muscle activation produces an efficient pumping action that not only squeezes blood out of the ventricles but produces kinetic energy as blood is accelerated from the ventricles. The result of conventional pacing is compromised Hemodynamics due to slow cell-to-cell conduction and an aberrant ventricular activation sequence as the cardiac conduction system is bypassed. The far-left ventricular wall away from the electrode site has been seen contracting against an already closed aortic valve.

For contextual understanding of how examples of the disclosure are intended to function, FIG. 1 is included to illustrate the structure of a typical human heart 1 with relevant anatomical features shown. As mentioned, one example of the disclosure is directed to a method for deploying an electrical lead to the LBB 5, potentially accessed from target site 10 on ventricular septum 3 from within the RV 12. Such a target site 10 for proper deployment of a pacing lead, is depicted in FIG. 1 against the wall of ventricular septum 3 below tricuspid valve septal leaflet 7 within RV 12. Targeting LBB 5 is particularly useful for patients experience LBB block. Examples may simultaneously target the LBB and RBB to facilitate dual bipolar, dual unipolar pacing, and/or cardiac resynchronization therapy. Nonspecific bundle branch pacing (conduction system and nearby myocardium) or contractile myocardium only pacing of either cathode may be appropriate in some cases.

In other examples, the target site may be the His bundle 2 at the septum 3 distal to the atrioventricular (AV) node 4, but proximal to the LBB 5 and the RBB 6. Such a target site for proper deployment of a pacing lead into the His bundle is at the crest of the ventricular septum 3 on the atrial aspect of the annulus of the tricuspid valve septal leaflet 7 within the right atrium 8.

Figure 2:
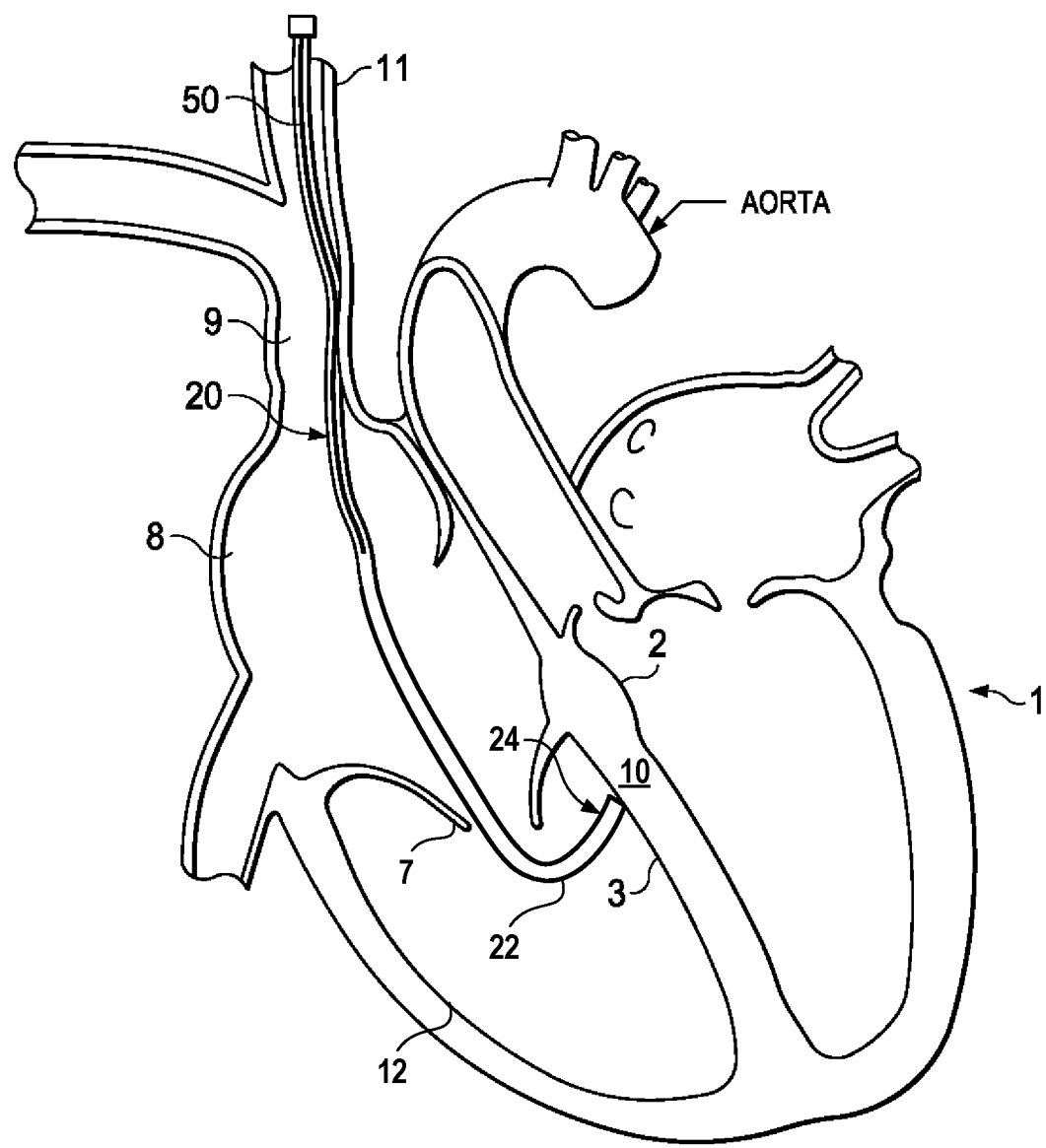
FIG. 2 is a cross-sectional illustration of a human heart wherein an example of a guide catheter is shown advanced to a target site within the RV corresponding to the RBB.

FIG. 2 is the schematic diagram of FIG. 1 in which a distal portion or end region 22 of delivery catheter 20 is shown extending into the RV 12 of the heart 1, from the superior vena cava 9 and the left subclavian vein 11, with the distal tip 24 positioned at the target site 10.

Typically, left pectoral side approach is desired. It involves accessing the heart via the left subclavian vein, the cephalic vein and more rarely the internal or external jugular vein, or femoral vein. However, it is also possible to utilize the less common right pectoral side approach. In either case, for catheter lead placement, a guide wire 50 may be advanced into the heart 1 from the access site. Delivery catheter 20 may be advanced through the vasculature and into the heart 1 over the guidewire; once in position pacing guidewire is removed. A pacing lead is then advanced through the guiding catheter 20 to be deployed at various regions in the heart.

Figure 3:
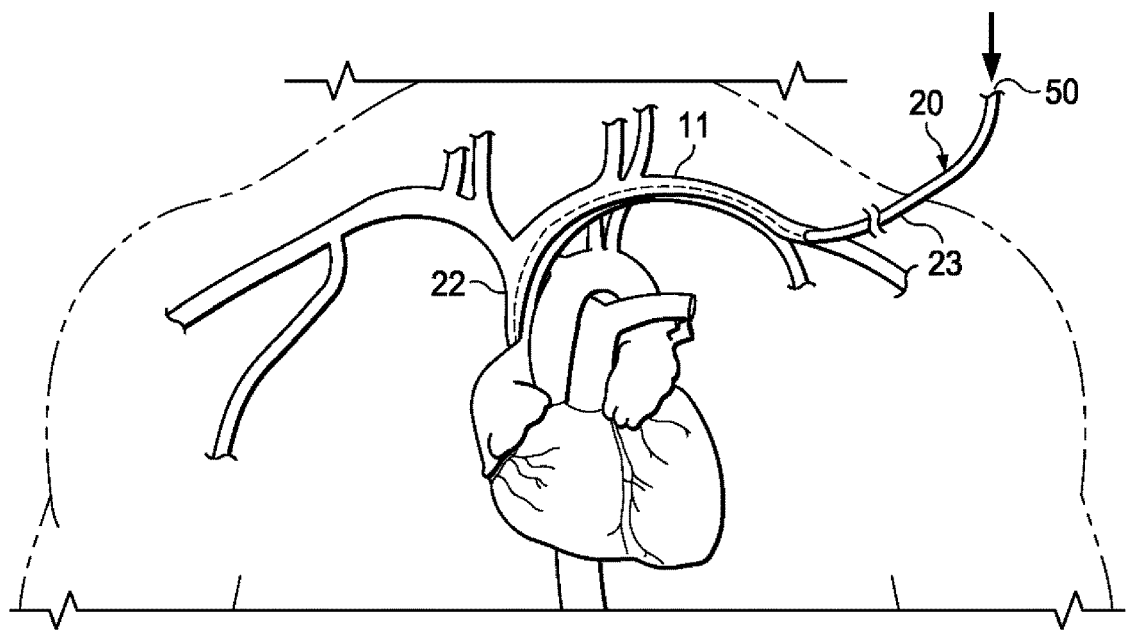
FIG. 3 is an anatomical illustration of a patient and the manner in which the example shown in FIG. 2 initially accesses the vasculature prior to advancement into the heart.

According to one method, a clinician positions guide wire 50 into the heart 1, for example via a "sub-clavian stick" or central venous access procedure such as is illustrated in FIG. 3. Accordingly, the catheter 20 is passed over the guide wire and advanced into the superior vena cava 9 from the left subclavian vein 11 through right atrium 8 and tricuspid valve septal leaflet 7 and into the RV 12 such as is in the manner shown in FIG. 2.

Figure 4:
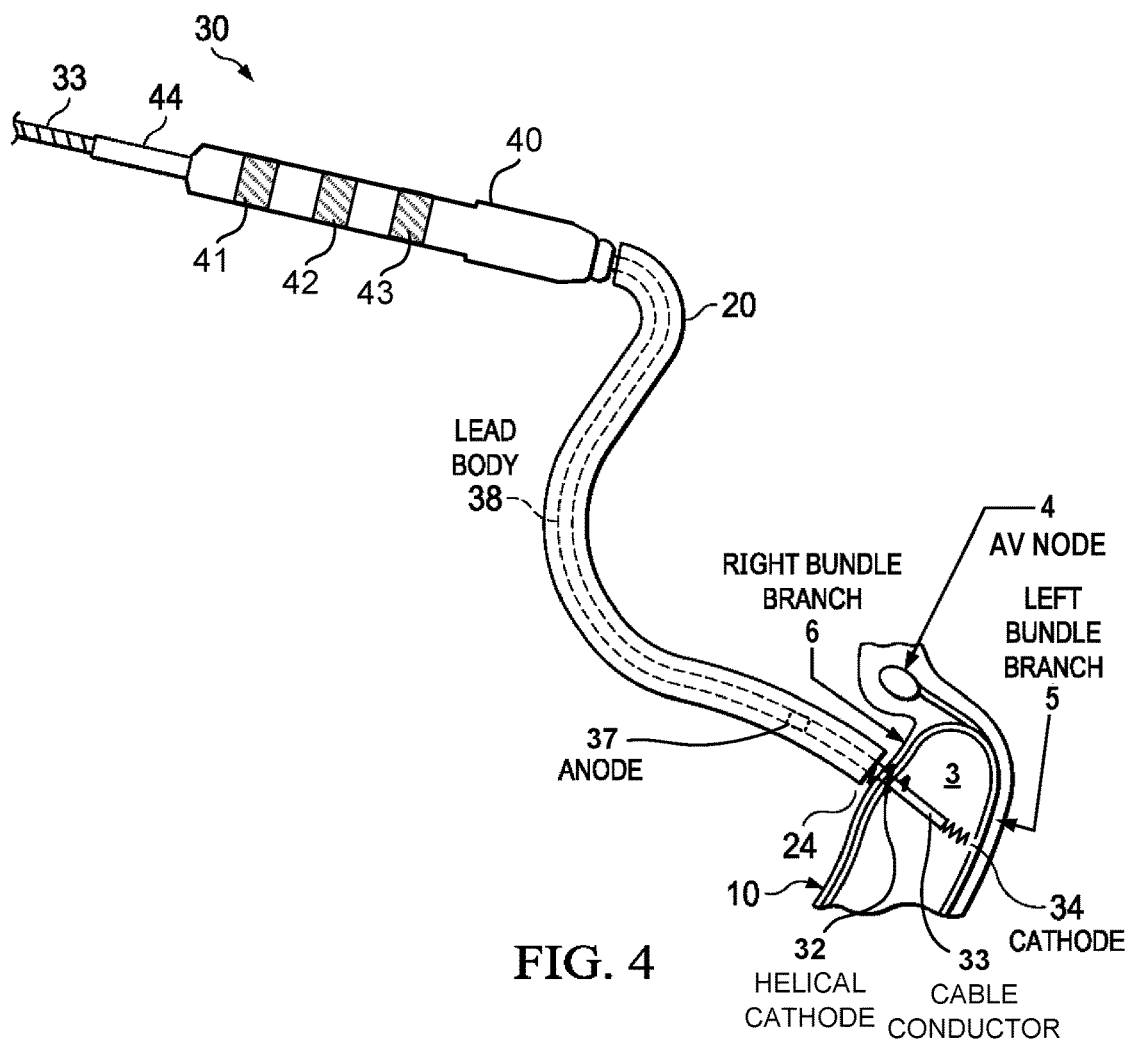
FIG. 4 is a conceptual illustration of a pacing lead accessing the septum from the RV in accordance with one example of this disclosure.

FIG. 4 illustrates a tripolar, or more specifically, a dual bipolar, medical electrical lead 30 in accordance with one example of this disclosure. Medical electrical lead 30 includes a helical electrode 32 and anode ring electrode 37, which are electrically coupled to connector terminal 41, and connector terminal 42, respectively. Medical electrical lead 30 further includes a central cable conductor 33 terminating at blunt cable helix 34 and extending within a central lumen of lead 30 about a length of lead body 38 for coupling to connector pin 44 of proximal connector 40.

Cable conductor 33 includes one or more conductive elements forming an electrical connection between blunt cable helix 34 and connector pin 44 once connector pin 44 is connected to the conductive elements of cable conductor 33. In various examples, cable conductor 33 may include a solid wire conductor, a stranded wire, or a coil conductor. In a particular example, cable conductor 33 may include a fiber core coil with one or more electrically conductive wires coiled on a fiber core. The fiber core may provide tensile strength for cable conductor 33 and mitigate stretching of the coiled conductors during retraction of cable conductor 33.

In the same or different examples, cable conductor 33 may be an insulated cable conductor including outer insulating layer, leaving the distal tip exposed for blunt cable helix 34. The insulating layer may include silicone rubber, polyurethane parylene, polymide and/or ethylene tetrafluoroethylene (ETFE) cable insulation. In some examples, connector pin 44 may be a self-stripping connector pin 44 to allow contact with the conductive elements of cable conductor 33. Alternatively, connector pin 44 may make electrical contact with conductive elements of cable conductor 33 upon tightening of a setscrew of the connector of a pulse generator or other device connected to proximal connector 40. Central cable conductor 33 is slidable the central lumen of lead body 38 to extend and retract blunt cable helix 34 relative to the distal end of lead body 38.

Blunt cable helix 34 extends across a width of the wire of the helix. While a variety of cable diameters may be used, relatively smaller diameters are best to facilitate blunt dissection with the blunt cable helix 34 for low force smooth advancement through the septum without rotation of cable conductor 33 and blunt cable helix 34. More specifically, the wire diameter of the cable helix may be within a range of 0.002 inches to 0.010 inches, such as a range of 0.003 inches to 0.007 inches, such as about 0.005 inches.

In some examples, the blunt cable helix 34 has a coil diameter of 0.5 to 2.0 mm, such as 0.7 to 1.0 mm diameter, at the end of an insulated blunt cable helix conductor of the same diameter in order to provide blunt dissection. More specifically, the coil diameter of the cable helix may be within a range of 1 French (0.013 inches) to 3 French (0.039 inches), such as a range of 1.5 French (0.020 inches) to 2.5 French (0.033 inches).

Helix 34 may be of any number of turns sufficient to provide fixation, such as 0.5 to 2 turns. Fewer turns mitigates risk of puncturing through the septum. The following materials may be utilized for the helix 34 wire: Pt 80%/Ir 20% or Pt 90%/Ir 10% for a thinner wire.

While a standard fixation helix includes a sharp tip with a single or double bevel, such as a 15 degree bevel, the blunt cable helix 34 includes a rounded or flat tip. For example, helix 34 may have such a sharpened tip. In contrast, the blunt tip of the blunt cable helix 34 may include a rounded or flat frontal surface extending across a width of the helix wire. In some examples, a thickness of the blunt tip is at least one-half of the width of the helix wire as measured proximal to a distal tip at an offset equal to the width of the helix wire, such as at least 75 percent of the width of the helix wire as measured proximal to the distal tip at the offset equal to the width of the helix wire.

The blunt tip of the blunt cable helix 34 is not meant to penetrate the tough endocardial membrane. Instead, it is designed to impinge on the left ventricular (LV) endocardial membrane and anchor the electrode without perforating the membrane. This is achieved through blunt dissection, where the blunt cable helix 34 is advanced through the septum without rotation. Once the blunt cable helix 34 has reached the target site, potentially confirmed with test stimulation, it is then rotated for fixation at the target site, such as the left bundle branch (LBB).

In the same or different examples, blunt cable helix 34 may be a unitary component with the conductive element(s) of cable conductor 33 or may be a separate component physically and electrically coupled to the distal end of the conductive element(s) of cable conductor 33, for example, by solder or welding, such as laser welding. In the same or different examples, the electrode proximate the distal end of cable conductor 33 may be a ring electrode instead of a tip electrode (such as electrode 535 of lead 530 in FIG. 11).

Medical electrical lead 30 includes a second conductor within lead body 38 extending between ring terminal 41 and anode ring electrode 37. Medical electrical lead 30 further includes a third conductor within lead body 38 extending between ring terminal 42 and helical electrode 32. In some examples, the second conductor and the third conductors are coaxial, insulated coil conductors surrounding the central cable conductor 33 within the lead body 38. The insulation should be selected to provide low friction with the central cable conductor 33. For example, the insulation of the coil conductors may be a low friction polymer material, such as silicone rubber, polyurethane, parylene, polymide and/or ETFE or other non-conductive material. Likewise, central cable conductor 33 may be insulated with a low-friction material or include a low-friction coating, such as silicone rubber, polyurethane, parylene, polymide and/or ETFE.

Helical electrode 32 may be made from a wire, such as a platinum alloy or other biocompatible metal. The number of turns and length of the helix may be adapted for a particular application. For example, helical electrode 32 may have 1 to 8 turns, such as 2 to 4 turns to support adequate fixation within patient tissue. A septal thickness can be anywhere from 0.9 to 1.2 centimeters in normal individuals. A risk of perforation will likely go up if the helix is too long and the entire helix penetrates the septum. Accordingly, the dimensions of the helix should be selected to allow fixation and capture of the RBB but mitigate a risk of perforation. In the present example, a helix length of 1.0 to 8.0 mm may be appropriate to mitigate a risk of piecing the septum, such as a helix length of 1.5 to 4 mm, such as about 1.8 mm. As used herein, the term about means within a range of tolerances of manufacturing techniques used to produce the referenced element.

Anode ring electrode 37 is coplanar with an outer surface of lead body 38. The spacing and surface area of anode ring electrode 37 is selected to provide support stimulation via both helical electrode 32 and blunt cable helix 34. In some examples, anode ring electrode 37 may have a spacing of between 5 to 15 mm from helical electrode 32, such as a spacing of between 7 to 10 mm, such as a spacing of about 9 mm. In the same or different examples, anode ring electrode 37 may have a surface area of between 10 to 30 square mm, such as a surface area of between 15 to 20 square mm, such as a surface area of about 16.9 square mm.

In one particular example of lead 30, the following dimensions may be used. Lead body 38 diameter 3 to 6 French, such as about 4.1 French, cable conductor 33 diameter, 0.02 to 0.05 inches, such as about 0.028 inches, helical electrode 32 length 1 to 4 mm, such as about 1.8 mm, helical electrode 32 pitch, 0.5 to 2 mm, such as about 1 mm, helical electrode 32 wire diameter 0.1 to 1.0 mm, such as about 0.3 mm. In the same or different examples, a platinum alloy may be utilized for the helical electrode 32 wire such as Pt 80%/Ir 20% or Pt 90%/Ir 10% for a thinner wire.

As used herein, the terms anode and cathode merely represent example uses of particular lead electrodes. For example, anode ring electrode 37, helical electrode 32, and blunt cable helix 34 are electrically isolated within medical lead 30 such that such that any two of anode ring electrode 37, helical electrode 32, and blunt cable helix 34 may form an electrode pair to deliver stimulation. However, the polarity of the stimulation is controlled by a pulse generator and not inherent to the structure of electrical lead 30 itself. Thus, the pulse generator could reverse the polarity of anode ring electrode 37, helical electrode 32, and blunt cable helix 34, use any two electrodes as an anode-cathode pair, or even use one or more of anode ring electrode 37, helical electrode 32, and blunt cable helix 34 in a unipolar configuration in combination with the pulse generator housing.

In FIG. 4, a close-up view of the distal tip 24 of the catheter 20 is shown following advancement of medical electrical lead 30 though a lumen of the catheter 20 to the target site 10. In this example, the target site for blunt cable helix 34 is the LBB, although the His bundle can also be targeted.

The lead 30 is extended distally from catheter distal tip 24, exposing helical electrode 32. At this point, the clinician may map of the RBB with the helical electrode 32 evaluate capture threshold. If desired, the clinician may adjust the position of the distal tip 24 of the catheter 20 adjacent the septal wall to improve capture of the RBB before proceeding to anchor the helical electrode 32.

The lead 30 is anchored into the septum 3 by clockwise rotation of the lead body 38 targeting the RBB, so that helical electrode 32 screws through the endocardial membrane and into the septal wall. The clinician may again map of the RBB with the helical electrode 32 to confirm capture threshold. If desired, the clinician may adjust the position of helical electrode 32 within the septal wall to improve capture of the RBB before proceeding to extend blunt cable helix 34.

The blunt cable helix 34 is extended into the septum 3 to provide pacing to the heart 1 via the LBB. The blunt cable helix 34 punctures the endocardial membrane in the center of helical electrode 32. In some examples, cable conductor 33 and blunt cable helix 34 may enlarge the perforation in the endocardial membrane created by helical electrode 32. In other examples, cable conductor 33 may be withdrawn from lead body 38 and a needle or stylet (not shown) may be used to puncture the endocardial membrane. In further examples, RF energy may be applied to cable conductor 33 to cross the RV endocardium, then detaching the RF connection to cable conductor 33 and advance it to the LV endocardium. No matter the technique used to puncture the endocardial membrane, blunt cable helix 34 pushes through septal tissue using blunt dissection. With the blunt cable helix 34 targeting the LBB, the helical electrode 32 is proximate the RBB, facilitating cardiac resynchronization therapy by independently activating helical electrode 32 and blunt cable helix 34.

The use of a stylet or needle may be particularly advantages for puncturing tissues with more toughness than the septal wall within the right atrium. For example, if targeting the His bundle from the right ventricle, a stylet or needle may be used to penetrate the central fibrous body. In one contemplated example, a clinician may first target the His bundle from the septal wall within the right atrium.

While blunt cable helix 34 is the preferred configuration of cable conductor 33 for use in septal implantation, other configurations of cable conductor 33 are also possible, including a pointed tip instead of blunt cable helix 34.

Figure 5A:
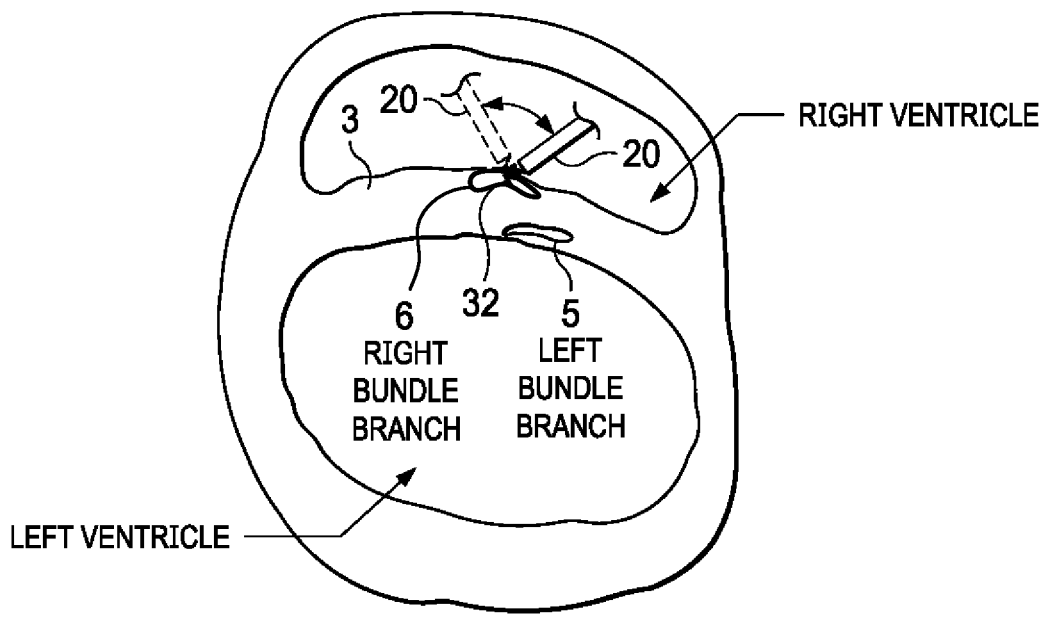
FIGS. 5A-5C illustrate detailed views of the distal region and tip of the pacing lead while mapping the LBB while attached to and fixed in a patient's septum.
Figure 5B:
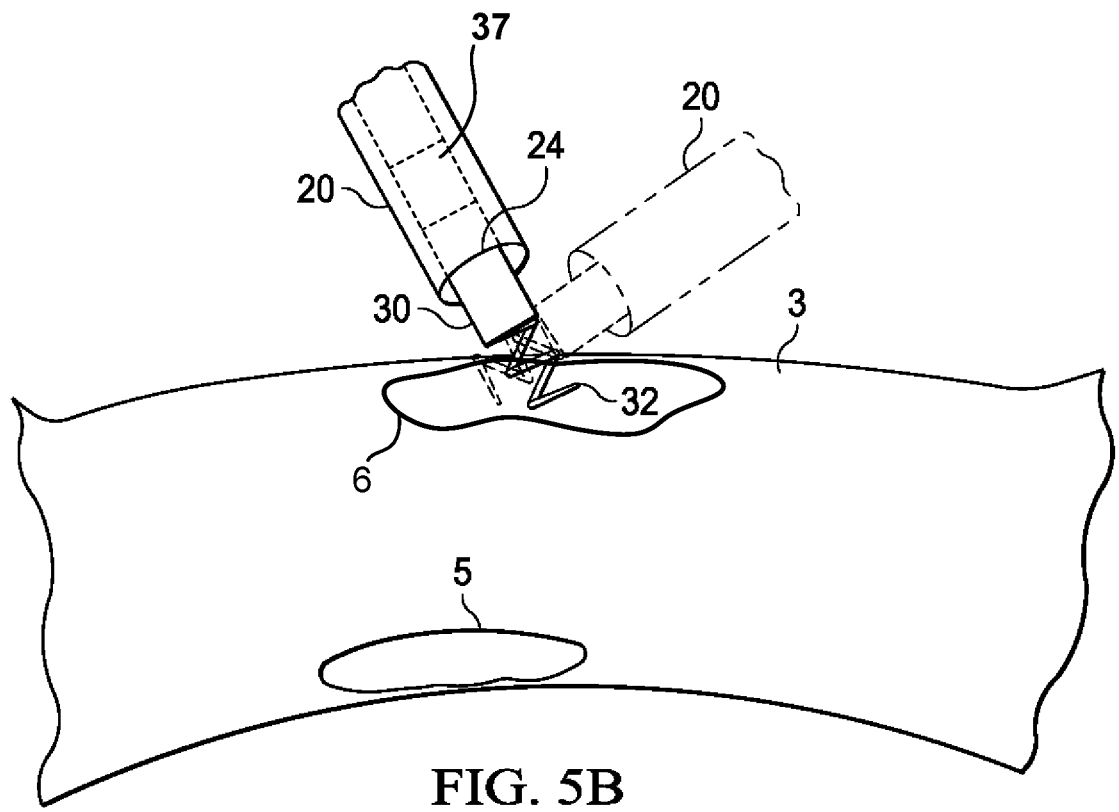
Figure 5C:
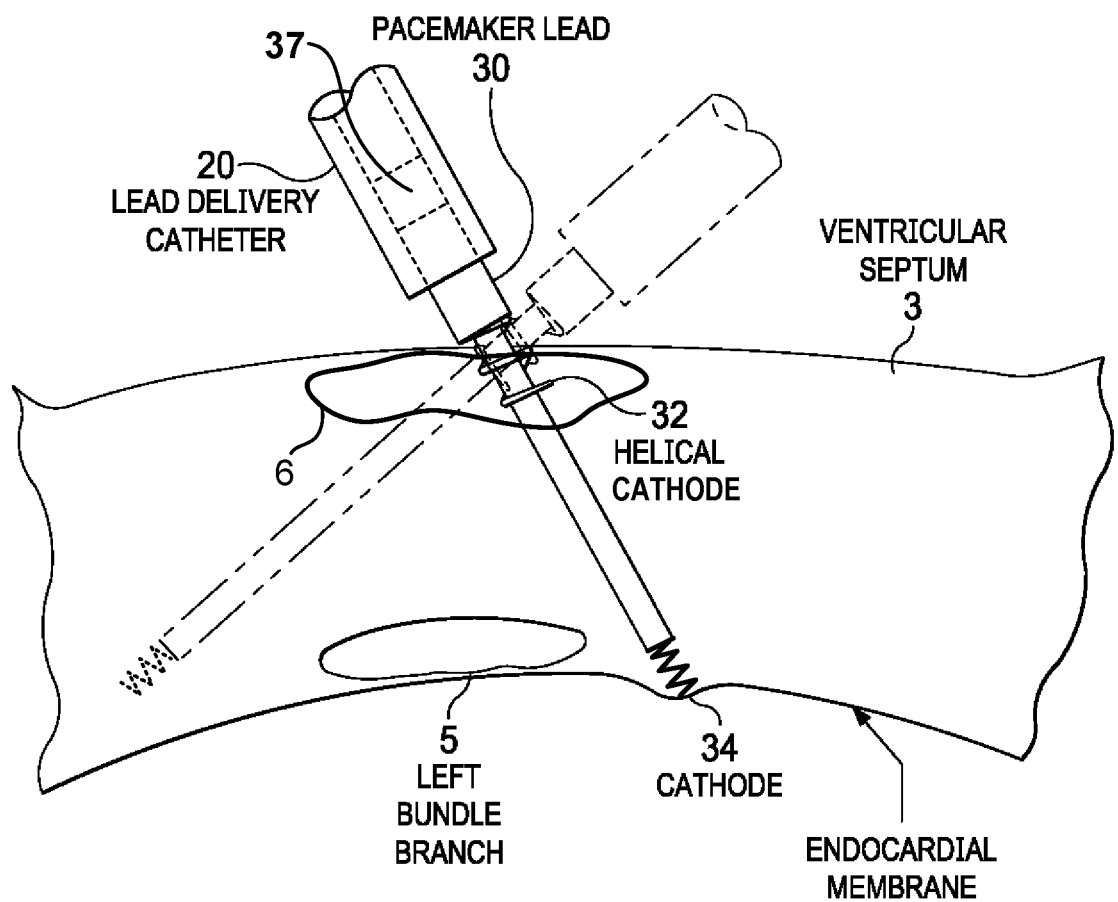

FIGS. 5A-5C illustrate detailed views of the distal region and tip of the pacing lead at a target site in a patient's septum. Specifically, FIG. 5A shows the trajectory of the blunt cable helix direction for mapping of the LBB during catheter introduction of the lead 30, while FIG. 5B shows a closeup of the lead delivery catheter and lead tip. The helical electrode 32 for lead attachment is shown anchored and is pivoted by the lead delivery catheter.

FIG. 5C shows the LBB mapping process and possible range of blunt cable helix location. Mapping for lead location is accomplished by sensing the LBB potential and/or pacing the LBB to produce a narrow QRS on the surface ECG, typical of physiologically normal ventricular activation. The trajectory of the blunt cable helix advancement is controlled by manipulation of the lead delivery catheter. Resistance to advancement of cable conductor 33 is felt when the electrode 34 impinges on the tough left ventricular endocardial membrane. See the tenting effect of the opposite endocardial membrane in FIG. 5C.

Figure 6:
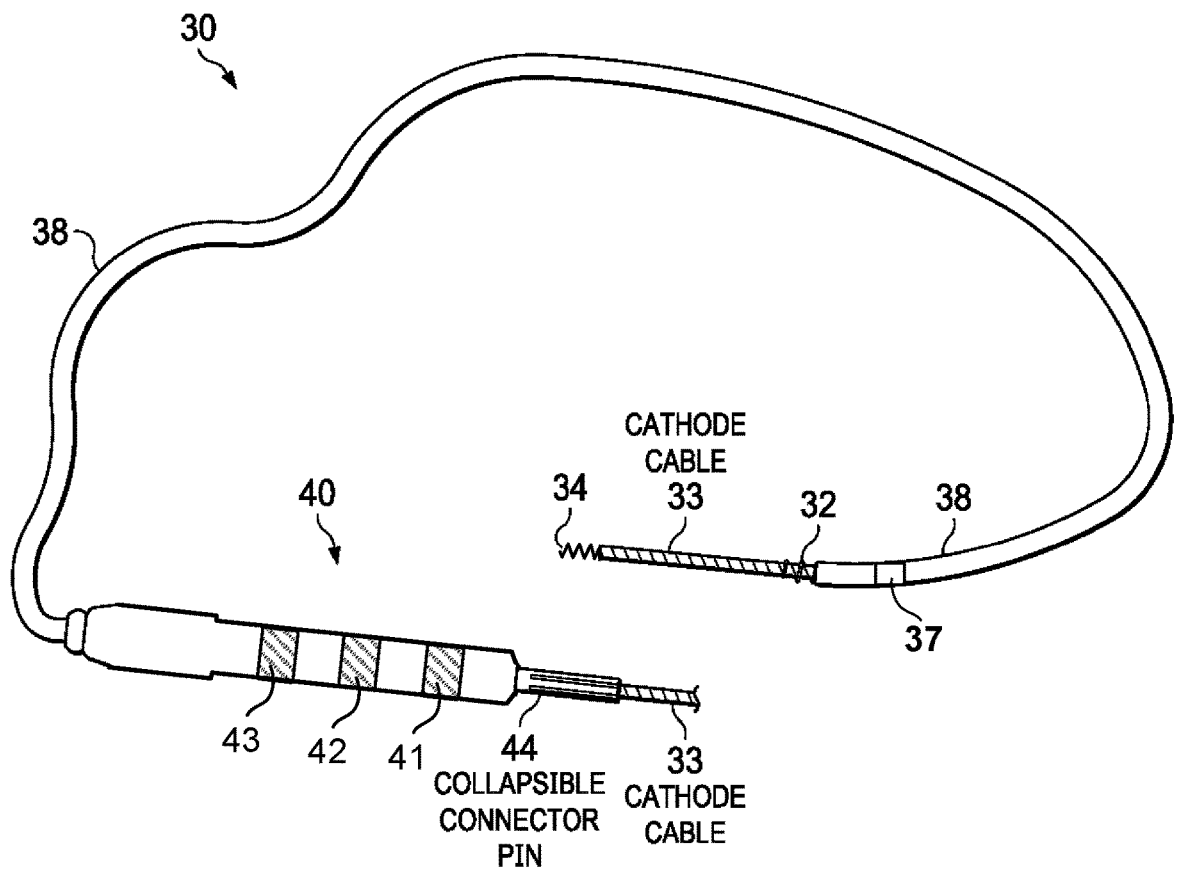
FIG. 6 illustrates the pacing lead with the proximal blunt dissection conductor and a self-stripping connector pin.

FIG. 6 illustrates lead 30 including a proximal connector 40 with a self-stripping connector pin 44. After selecting a proper lead position in the heart, cable conductor 33 is cut flush with the connector pin 44. The pulse generator's connector setscrew is tightened to make electrical contact, fracturing the cable insulation, and completing the circuit to blunt cable helix 34. The setscrew also fixes the relative position of cable conductor 33 to proximal connector 40. Also illustrated is proximal ring terminals 41, 42, 43 located adjacent and distal to connector pin 44. Ring terminal 41 provides an electrical connection to anode ring electrode 37, while ring terminal 42 provides an electrical connection to cathode electrode 32. Ring terminal 43 may provide a redundant connection to one of electrodes 34, 32, 37 or a connection to an optional fourth electrode (not shown), such as a second distal electrode on lead body 38, either proximal or distal to electrode 37.

In other examples, a proximal end of cable conductor 33 may include an exposed conductor the same diameter as the pin electrode of an IS-4 connector, or other industry standard connector. In such examples, the exposed conductor may simply be cut to the proper length after extending blunt cable helix 34 to the target site. In such examples, collapsible connector pin 44 is not required as the exposed proximal end of cable conductor 33 itself serves as the pin electrode of connector 40. The pulse generator's connector setscrew secures the position of cable conductor 33 relative to the connector body.

The example proximal connector 40 illustrated in FIG. 6 conforms to the IS-4 standard. In various examples, connector 40 may conform to a standard pulse generator connector, such as an IS-1, IS-4, DF-1, DF-4, or other industry standard connector.

Figure 7A:
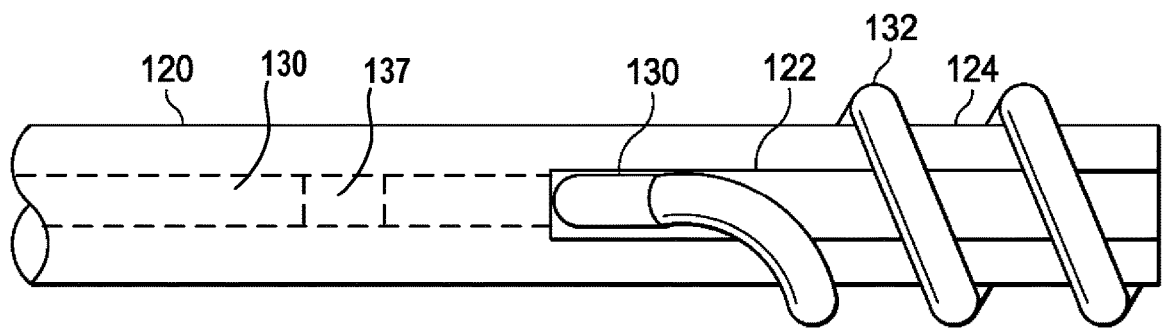
FIGS. 7A-7C illustrate an alternative lead design with an exposed helical electrode that facilitates mapping.
Figure 7B:
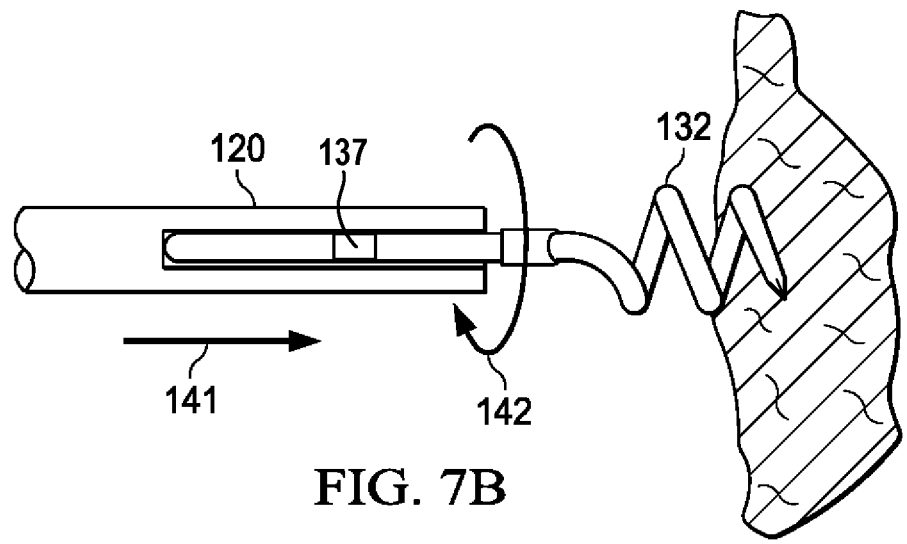
Figure 7C:
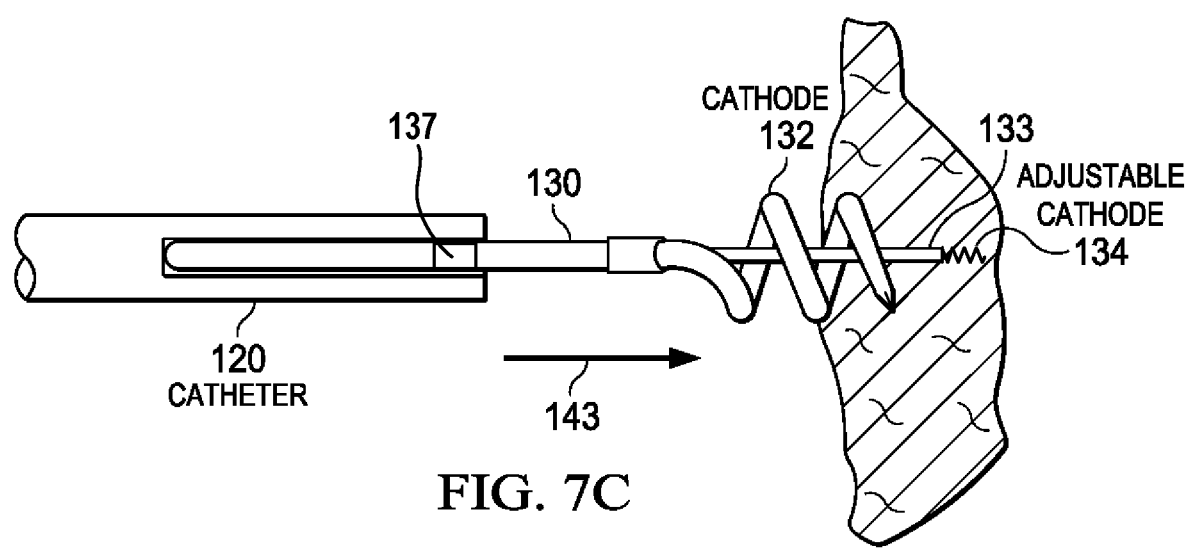

FIG. 7A-7C illustrate the distal end of a medical electrical lead 130, which provides an alternative lead design as compared to medical electrical lead 30. With this example, a helical electrode 132 is attached over the lead delivery catheter tip 124. This exposes the helical electrode 132 for mapping purposes. As shown in FIG. 7A, helical electrode 132 extends through slot 122 which extends along a length of delivery catheter 120 at lead delivery catheter tip 124. The pointed distal tip of helical electrode 132 is closely fitted to the catheter outer diameter to prevent snagging on intervascular tissue during venous passage of the catheter lead assembly. Deployment of helical electrode 132, e.g., through extension of cable conductor 133 in direction 141, then turning lead 130 relative to the patient tissue in direction 142 (corresponding to the curvature of helical electrode 132) anchors the distal tip of helical electrode 132 in the patient tissue.

Similar to lead 30, lead 130 includes an anode ring electrode 137. Lead 130 also includes a blunt cable helix 134, the trajectory of which is selectable by a clinician by manipulating the catheter lead assembly after anchoring helical electrode 132 within a tissue of the patient, such as the septal wall. This design of catheter 120 and lead 130 may increase the percutaneous introduction size, such as by 2 French as compared to catheter 20 and lead 30. Following the selection of the trajectory, the clinician may deploy blunt cable helix 134 within the patient tissue along direction 143, representing the selected trajectory, through extension of cable conductor 133 by pushing cable conductor 133 relative to helical electrode 132 of lead 130.

Figure 8:
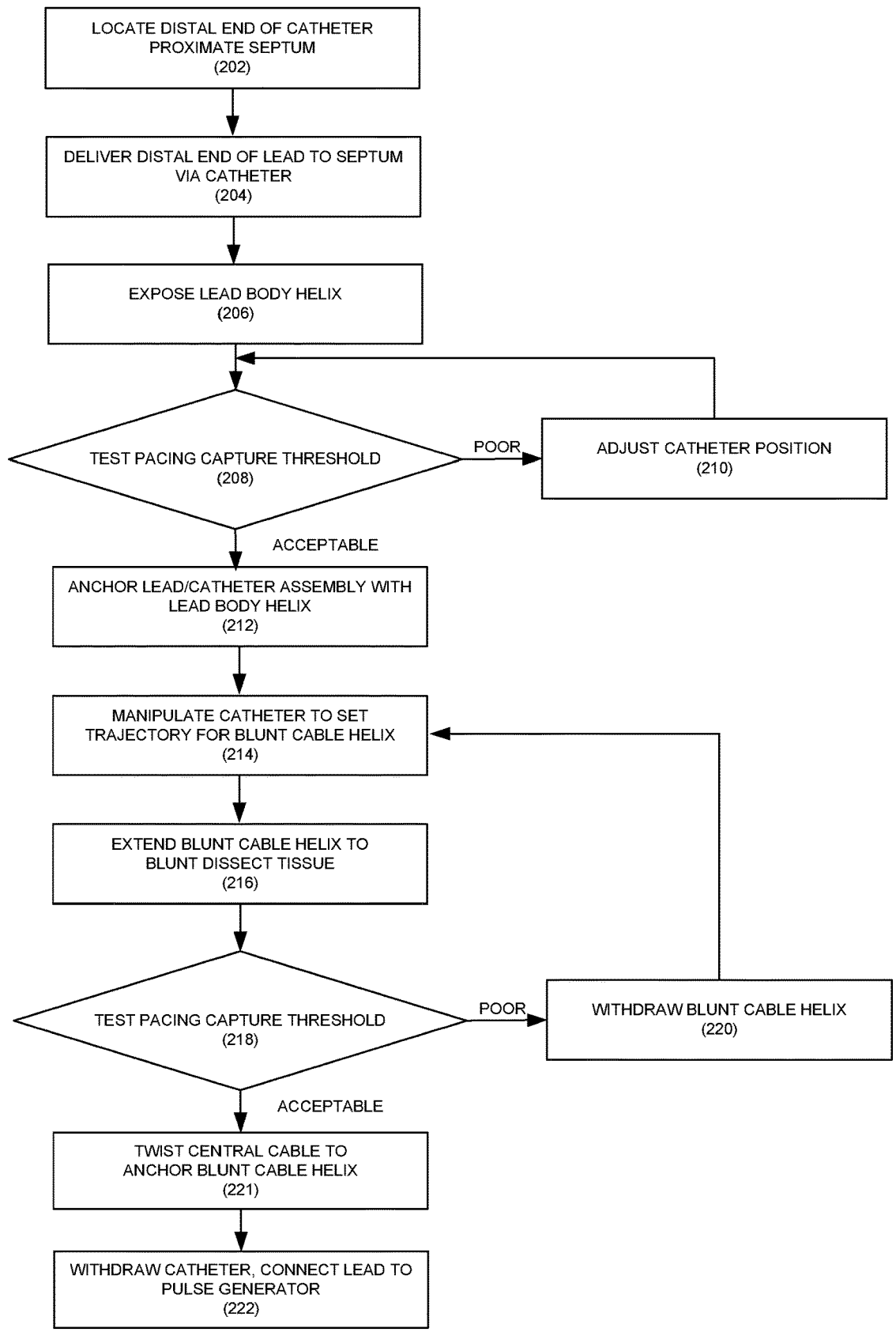
FIG. 8 is a flowchart illustrating techniques for locating a lead electrode proximate the LBB and RBB for cardiac resynchronization therapy.

FIG. 8 is a flowchart illustrating techniques for locating a lead electrode to pace the cardiac conduction system, to allow capture of both the RBB and LBB. For clarity, the techniques of FIG. 8 are described with respect to catheter 20 and medical electrical lead 30, although the techniques may likewise be applied to medical electrical leads 130, 330, 430, 530 and to variations of the example leads disclosed herein.

First, a clinician positions the distal tip 24 of catheter 20 at the target site 10 on a patient's septum within the RV (FIG. 8, step 202). In some example, a guidewire may be used to direct the catheter to target site 10. Once, the distal tip 24 of catheter 20 is positioned at the target site 10, the clinician removes guidewire (if any) and introduces lead 30 via the central lumen of the catheter 20. The distal end of lead 30 is delivered to the target site 10 in the septum via catheter 20 (FIG. 8, step 204). In other examples, lead 30 may be introduced with a stylet, after temporarily extracting the central cable conductor 33 from the central lumen of lead 30. The relatively stiff stylet may also be used by, blunt dissection, to clear a pathway through tough tissue such as the central fibrous body for His bundle pacing or along the left ventricular septum paralleling the LBB, especially when a relatively flexible cable conductor 33 is desirable.

For mapping, the clinician exposes the helical electrode 32 out the distal tip 24 of catheter 20 (FIG. 8, step 206). The clinician may test pacing capture threshold with helical electrode 32 (FIG. 8, step 208). For example, the clinician may test capture threshold of the RBB to find a suitable target site for the implantation. The clinician adjusts the location of the distal tip 24 of catheter 20 to select a target site for the implantation while testing pacing capture threshold with helical electrode 32 (FIG. 8, step 210).

The clinician anchors the catheter lead assembly to the target site 10 in the septum by rotating the lead 30 to engage the septum with the helical electrode 32 of lead 30 (FIG. 8, step 212). Preferably, to limit flouro time and trauma to patient tissue, helical electrode 32 is only anchored a single time, but the clinician may withdraw and anchor the helical electrode 32 if the pacing or sensing capture threshold is undesirable.

After securing the helix, the clinician may then manipulate the catheter 20 to set a desired trajectory for blunt dissection of the septum with the blunt cable helix blunt cable helix 34 (FIG. 8, step 214). For example, the clinician may select a trajectory for the blunt cable helix by manipulating the catheter after anchoring the helical electrode to the septal wall by bending the catheter through pushing and pulling from a proximal location outside the body of the patient, as well by rotating the catheter from the outside the body of the patient. Once helical electrode 32 is fixed to the septum, the septal wall is punctured and the blunt cable helix can be advanced, by blunt dissection between about 0.9 to 1.8 centimeters in an adult patient from the base of helical electrode 32, toward the LBB, just inside left ventricular septum (FIG. 8, step 216).

For mapping, the clinician may optionally withdraw the blunt cable helix 34 (FIG. 8, step 220), set a new desired trajectory, and redeploy the blunt cable helix 34. Generally, however, a clinician will only want to retract and redeploy the blunt cable helix 34 if sensing or pacing capture threshold is undesirable (FIG. 8, step 218). If mapping finds adjustment is necessary, blunt cable helix 34 is extracted to helical electrode 32 and helical electrode 32 can be pivoted to a desired new trajectory for advancement of cable conductor 33.

Once the blunt cable helix 34 has reached the target site, confirmed by mapping or test stimulation, rotating the cable conductor relative to the lead body to anchor the cable helix to the patient tissue, cable conductor 33 then rotated for fixation of the blunt cable helix 34 at the target site, such as the left bundle branch (LBB) FIG. 8, step 221). If further position adjustment in desired, the blunt cable helix 34 may be released by rotating in the opposite direction.

Examples may simultaneously target the LBB and RBB to facilitate dual bifocal, dual bipolar or unipolar pacing, for cardiac resynchronization therapy. Nonspecific bundle branch pacing (conduction system and nearby myocardium) or contractile myocardium only specific bundle branch pacing of either cathode may be appropriate in some cases.

Cathodal voltage stimulation of the LBB via blunt cable helix 34 and cathodal voltage stimulation of the RBB via helical electrode 32 can be independently adjusted to suit the LBB pacing voltage threshold and the RBB pacing voltage threshold independently to produce LV/RV synchrony. Alternatively, lead 30 may be operated to provide dual bifocal stimulation. In one example, the dual bifocal stimulation may operate ring electrode 37 as the anode and alternatively using blunt cable helix 34 and helical electrode 32 as cathodes. In another example, the dual bifocal stimulation may operate helical electrode 32 as the anode with and blunt cable helix 34 as the cathode alternated with operating ring electrode 37 as the anode with and helical electrode 32 as the cathode.

Blunt cable helix 34 forms a rounded or flat frontal surface extending across a width of the wire of the helix. In some examples, the blunt cable helix 34 is a 0.7 to 1 mm diameter helical electrode at the end of an insulated conductor of the same diameter in order to provide blunt dissection. Micro-dislodgement issues with other small pacing electrodes should be limited due to the embedded myocardial electrode placement of blunt cable helix 34 as opposed to placement on the endocardial surface as is the case for conventional tined leads. Thus, the disclosed techniques may mitigate instances of micro-dislodgement as can occur with electrodes positioned on the surface of a patient tissue.

In the same or different examples, the helix electrode 34 of cable conductor 33 may be coated with a steroid to mitigate scar tissue and its negative effects on capture threshold over time.

While lead 30 may optionally be used to target the His bundle from the right atrium, occasionally, His bundle pacing (at the crest of the ventricular septum and within the right atrium) cannot correct LBB block. LBB block cannot be corrected by His bundle pacing in as many as ten to twenty percent of patients due to infra-hisian block or other issues. When that happens, cable conductor 33 may be retracted and the trajectory of cable conductor 33 adjusted to target the LBB. Specifically, the clinician may target the LBB from with the right atrium without repositioning the anode helix, rather than from the RV as described previously. In such examples, the previously anchored anode helix can be pivoted about ninety degrees to align with the ventricular septum. When cable conductor 33 is advanced, blunt cable helix 34 slides along the endocardial membrane of the left ventricle, targeting the LBB, thereby bypassing the infra-hisian block.

When used for His pacing, particularly when the LBB block cannot be corrected at the His bundle due to distal block, blunt cable helix 34 is retracted. The catheter is rotated to a blunt cable helix trajectory that aims at the LBB. The blunt cable helix is then advanced along the left ventricular endocardial membrane to pace the LBB. In such examples, lead 30 may be used to apply bifocal stimulation to the LBB with electrode 34 and either of two electrodes 32, 37 or trifocal stimulation using all three electrodes 34, 32, 37. The blunt dissection tip mitigates the risk of puncturing the septal wall of the left ventricle. Such examples allow a clinician to first target the His bundle from the right atrium and adjust to the LBB if needed within limited flouro time.

Other advantages of targeting LBB and/or RBB, is that the LBB and RBB represent relatively big target areas, easing implantation of lead 30. In addition, threshold voltages may remain lower for the LBB and/or RBB stimulation compared to His bundle pacing. For this reason, clinicians may first target the LBB and/or RBB, without first targeting the His bundle.

Once the position of the blunt cable helix 34 is satisfactory, the clinician may withdraw catheter 20, cut the cable conductor 33 flush with connector pin 44, insert proximal connector 40 into the pulse generator's connector, and tighten the setscrew to cut through the insulation and complete the circuit (FIG. 8, step 222). In examples in which the pulse generator is an implantable pacemaker, the clinician then inserts the implantable pacemaker in a pocket under the skin in the patient's chest and is ready for sensing and/or pacing via the lead 30.

Figure 9:
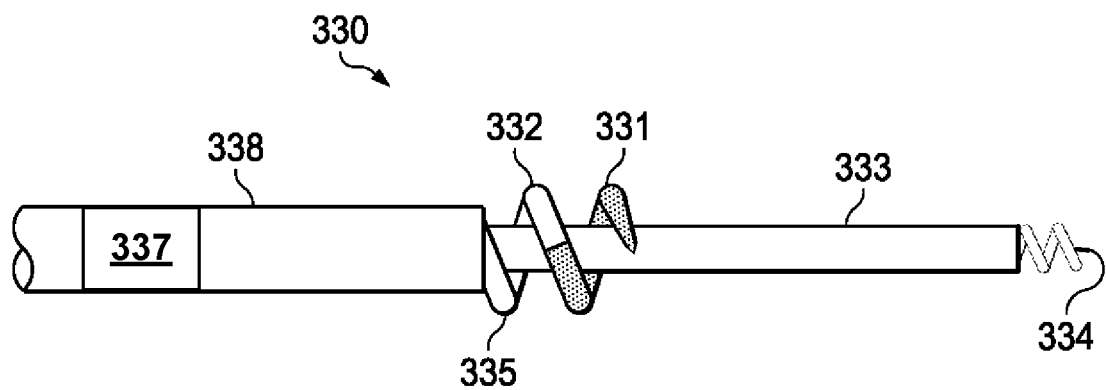
FIG. 9 illustrates an alternative lead design with a helix partially covered by an insulating layer.

FIG. 9 illustrates medical electrical lead 330. Lead 330 is substantially similar to lead 30 except that lead 330 includes an insulating layer 331 over the distal portion of helical electrode 332, partially covering helical electrode 332. The insulating layer 331 limits the exposed anode 335 surface area, increasing field density adjacent helical electrode 332 to allow for bifocal stimulation. In all other aspects, lead 330 is the same as lead 30. For brevity, details discussed with respect to lead 30 are discussed in limited or no detail with respect to lead 330.

Medical electrical lead 330 includes an anode ring electrode 337. Lead 330 also includes a central cable conductor 333 with blunt cable helix 334, and conductor for electrodes 332, 337. In some examples, the conductors for electrodes 332, 337 are coil conductor surrounding central cable conductor 333 within the lead body 338. In the same or different examples, the central cable conductor 333 may include an insulated conductor, such as a solid wire, a stranded wire, or a coil conductor.

Blunt cable helix 334 forms a rounded or flat frontal surface extending across a width of the wire of the helix. The insulating layer 331 over helical electrode 332 may be any suitable dielectric material, such as a polymer material, such as silicone rubber, polyurethane, parylene, polymide and/or ETFE or other non-conductive material.

The configuration of lead 330 provides reduced helical pacing current threshold compared to lead 30. Such a configuration may be particularly useful when right septal bifocal stimulation is desired for example. Such pacing may be useful to support LV/RV synchronization.

A ratio of anode to blunt cable helix surface area should be selected to support bipolar pacing. In some examples, the anode to blunt cable helix area ratio should be in 2:1 to 30:1, such as 4:1 to 20:1, such as about 16:1. In one particular example of lead 330 the following dimensions may be used. Lead 330 diameter 5 French, cable conductor 333 diameter 0.9 mm, helical electrode 332 length 1.8 mm, helical electrode 332 pitch 1 mm, helical electrode 332 wire diameter 0.3 mm, blunt cable helix 334 surface area 1.2 mm$^2$, exposed anode 335 surface area 20 mm$^2$.

Figure 10:
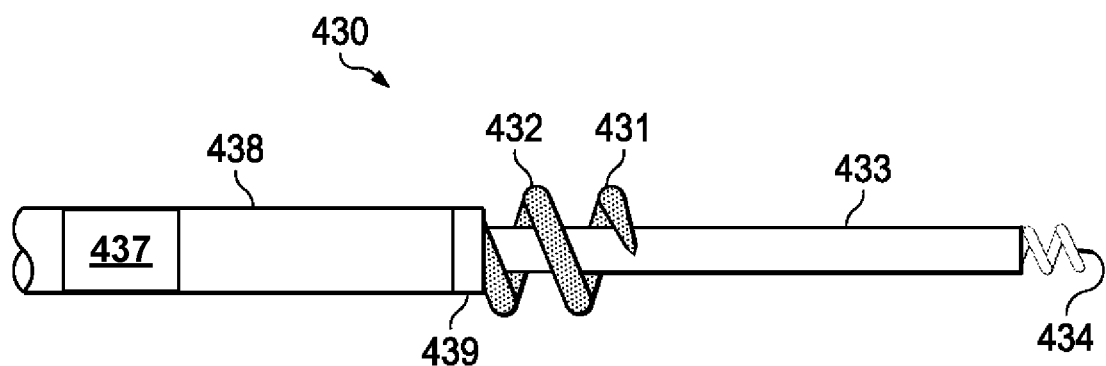
FIG. 10 illustrates an alternative lead design with an insulated helix fully covered by an insulating layer and a cathode ring on the distal end of the lead body.

FIG. 10 illustrates medical electrical lead 430. Medical electrical lead 430 includes an insulating layer 431 fully covering portion of helix 432. Medical electrical lead 430 further includes a ring electrode 439 on the distal end of lead body 438. In some examples, helix 432 is laser welded to ring electrode 439. In other examples, ring electrode 439 may be on a distal portion of lead body 438, but not necessarily on the distal tip of lead body 438. In the same or different examples, ring electrode 439 may be a partial ring electrode. Lead 430 is otherwise substantially similar to lead 30.

In the configuration of medical electrical lead 430, ring electrode 439 may serve as the second cathode and/or an anode to provide bipolar stimulation in combination with blunt cable helix 434. In all other aspects, lead 430 is the same as lead 30. For brevity, details discussed with respect to lead 30 are discussed in limited or no detail with respect to lead 430.

Medical electrical lead 430 includes an anode ring electrode 437 proximal to proximal to helix 432. Lead 430 also includes a central cable conductor 433 for a blunt cable helix 434, as well as a conductors for electrodes 437, 439. In some examples, the conductors for electrodes 437, 439 are coaxial, insulated coil conductors surrounding the central cable conductor 433 within the lead body 438. In the same or different examples, the central cable conductor 433 may include an insulated conductor, such as a solid wire, a stranded wire, or a coil conductor.

Blunt cable helix 434 forms a rounded or flat frontal surface extending across a width of the wire of the helix. The insulating layer 431 may be any suitable dielectric material, such as a polymer material, such as parylene, polymide or other non-conductive material.

Like lead 330, the configuration of lead 430 provides reduced helical current pacing threshold compared to lead 30. Such a configuration may be particularly useful when right septal bipolar stimulation is desired for example. A ratio of anode (such as ring electrode 437) to blunt cable helix surface area should be selected to support bifocal pacing. In some examples, the anode to blunt cable helix area ratio should be in 2:1 to 30:1, such as 4:1 to 20:1, such as about 16:1.

Such pacing may be useful to support LV/RV synchronization. For example, cathodal voltage stimulation of the LBB via blunt cable helix 434 and cathodal voltage stimulation of the RBB via electrode 439 can be independently adjusted to suit the LBB pacing voltage threshold and the RBB pacing voltage threshold independently to produce LV/RV synchrony. Alternatively, lead 430 may be operated to provide dual bifocal stimulation. In one example, the dual bifocal stimulation may operate ring electrode 437 as the anode and alternatively using blunt cable helix 434 and ring electrode 439 as cathodes. In another example, the dual bifocal stimulation may operate ring electrode 437 as the anode with and blunt cable helix 434 as the cathode alternated with operating ring electrode 437 as the anode with and ring electrode 439 as the cathode.

The configuration of lead 430 is also suitable for His bundle pacing near the endocardial surface by prevention of blunt cable helix shorting to the helical electrode as may occur with lead 30. Specifically, the location of ring electrode 439 provides further separation between ring electrode 439 and distal blunt cable helix 434 by the endocardial membrane. Such a configuration may mitigate short circuiting of the electrodes even with a shallow blunt cable helix placement. Such placement may be particularly useful when the His bundle presents near the endocardium as a shallow blunt cable helix placement would position the blunt cable helix adjacent the His bundle.

Figure 11:
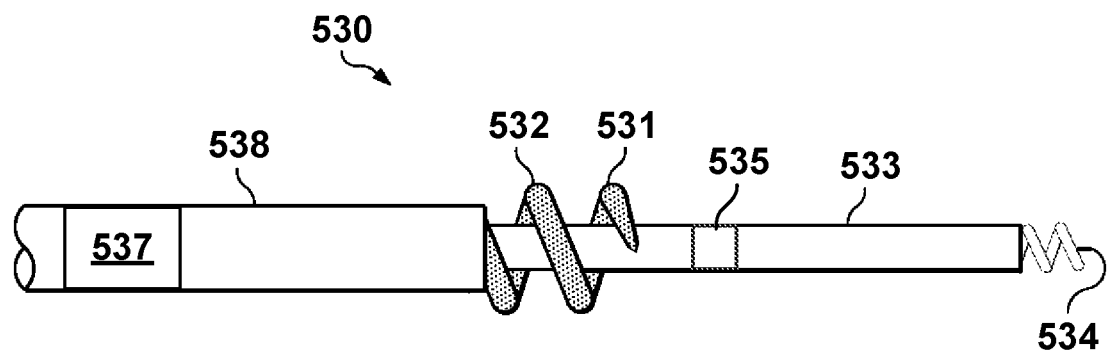
FIG. 11 illustrates an alternative lead design including two cable electrodes.

FIG. 11 illustrates medical electrical lead 530. Medical electrical lead 530 includes a ring electrode 535 on the cable conductor 533. Medical electrical lead 530 also includes an optional insulating layer 531 fully covering a portion of helix 532. Lead 530 is otherwise substantially similar to lead 30.

In the configuration of medical electrical lead 530, ring electrode 535 may serve as the second cathode and/or an anode to provide bifocal stimulation in combination with blunt cable helix 534. In all other aspects, lead 530 is the same as lead 30. In addition, central cable conductor 533 includes two conductors, one for ring electrode 535, and one for blunt cable helix 534. For brevity, details discussed with respect to lead 30 are discussed in limited or no detail with respect to lead 530.

Medical electrical lead 530 includes an anode ring electrode 537 proximal to helix 532. Lead 530 also includes a central cable conductor 533 for a blunt cable helix 534. In such examples, central cable conductor 533 includes at least two insulated conductors and at least two proximal contacts. In some examples, the central cable conductor 533 including solid wire, stranded wire, or coiled conductor. In the same or different examples, the anode conductor is a coil conductor surrounding the central cable conductor 533 within the lead body 538.

Blunt cable helix 534 forms a rounded or flat frontal surface extending across a width of the wire of the helix. The insulating layer 531 may be any suitable dielectric material, such as a polymer material, such as parylene, polymide or other non-conductive material.

Like lead 330, the configuration of lead 530 provides reduced bipolar current pacing threshold compared to lead 30. Such a configuration may be particularly useful when right septal bifocal stimulation is desired for example. A ratio of anode (ring electrode 537) to blunt cable helix surface area should be selected to support bifocal pacing. In some examples, the anode to blunt cable helix area ratio should be in 2:1 to 30:1, such as 4:1 to 20:1, such as about 16:1.

Such pacing may be useful to support LV/RV synchronization. For example, if electrode 535 and blunt cable helix 534 are designed to have a similar pacing capture voltage, the LBB can be stimulated at the same time as the right septal myocardial (or right bundle if it were viable and in range of the anode) to promote LV/RV synchrony. Alternatively, lead 530 may be operated to provide dual bifocal stimulation. In one example, the dual bifocal stimulation may operate ring electrode 537 as the anode and alternatively using blunt cable helix 534 and ring electrode 535 as cathodes. In another example, the dual bifocal stimulation may operate ring electrode 535 as the anode with and blunt cable helix 534 as the cathode alternated with operating ring electrode 537 as the anode with and ring electrode 535 as the cathode.

In a variation of lead 530, helix 532 may include an uninsulated portion forming a helical electrode, such that lead 530 includes four different electrodes: 532, 534, 535, and 537, each connected to an individual electrode in the proximal lead connector, which may conform to the IS-4 standard. For example, cable conductor 533 may include two insulated conductors, one for each of electrodes 534, 535. In such an example, connection to the proximal connector may occur by ring or split ring contacts. The four electrodes 534, 535, 532 and 537 may be used in any combination to provide stimulation and/or sensing. Such flexibility may allow a clinician to adjusting electrode combinations and/or stimulation parameters to account for scarring or lead migration, not only at the time of implantation of such a lead, but also in the months and years following implantation without the need for surgical intervention.

In further examples, cable conductor 533 may include a plurality of ring electrodes, such as two to ten electrodes. In such examples, cable conductor 533 may include a corresponding number of insulated conductors extending to individual electrical contacts at the proximal end of cable conductor 533. In one example, the individual electrical contacts may include ring electrodes, and/or partial ring electrodes and an optional pin electrode. Including more electrodes in lead 530 and cable conductor 533 will generally require a larger lead diameter to account for the additional conductors. In any of the examples described with respect to lead 530, two or more electrodes may also share a conductor such that they are operated jointly to provide stimulation or sensing.

Figure 12:
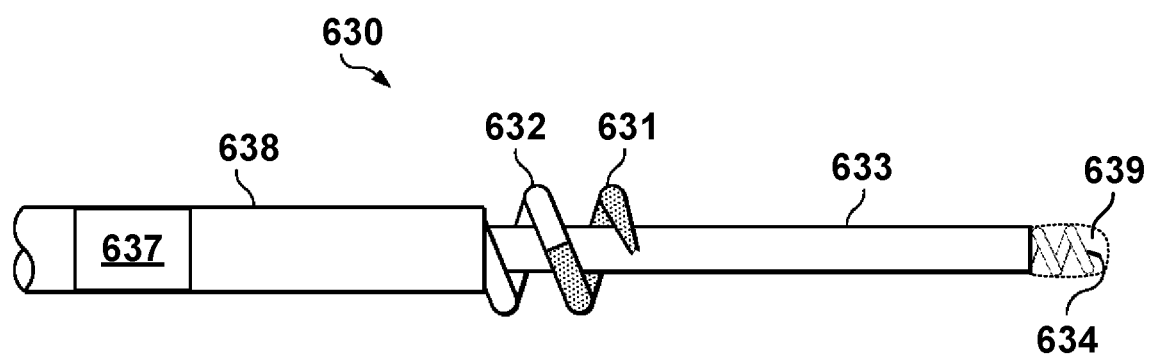
FIG. 12 illustrates an alternative lead design including a cable helix is encased in a coating of mannitol, the mannitol forming a blunt tip at the distal end of the cable.

FIG. 12 illustrates medical electrical lead 630. Cable helix 634 is encased in a coating of mannitol 639, the mannitol 639 forming the blunt tip at the distal end of the cable conductor 633. Medical electrical lead 630 also includes an optional insulating layer 631 partially covering portion of helix 632. Lead 630 is otherwise substantially similar to lead 30.

In the configuration of medical electrical lead 630, the mannitol 639 forms a blunt tip at the distal end of the cable conductor 633. In such a configuration, cable helix 634 may include its own blunt tip or may include a standard beveled tip. In all other aspects, lead 630 is the same as lead 30. For brevity, details discussed with respect to lead 30 are discussed in limited or no detail with respect to lead 630.

Upon delivery to a target site, once exposed to fluids within a body cavity, mannitol 639 melts within several minutes, exposing cable helix 634 to facilitate direct fixation with cable helix 634 by rotating cable conductor 633. In various examples, the wire of cable helix 634 may include a blunt or sharp tip, a blunt tip may mitigate undesired perforation if cable helix 634 is used for blunt dissection after mannitol 639 melts, whereas a sharp tip may reduce the rotation force required for direct fixation with cable helix 634 by rotating cable conductor 633.

Medical electrical lead 630 includes an anode ring electrode 637 proximal to helix 632. Lead 630 also includes a central cable conductor 633 for a blunt cable helix 634. In some examples, the central cable conductor 633 includes solid wire, stranded wire, or coiled conductor. In the same or different examples, the anode conductor is a coil conductor surrounding the central cable conductor 633 within the lead body 638.

The mannitol 639 forms a rounded or flat frontal surface extending across a width of the cable. In some examples, the mannitol 639 is 0.5 to 2 mm diameter, such as 0.7 to 1 mm diameter hemisphere, such as a half sphere with a diameter of about 0.87 mm, at the end of an insulated blunt cable helix conductor of a similar diameter in order to provide blunt dissection. More specifically, the diameter of the rounded or flat frontal surface of mannitol 639 may be within a range of 1 French (0.013 inches) to 3 French (0.039 inches), such as a range of 1.5 French (0.020 inches) to 2.5 French (0.033 inches).

Helix 634 may be of any number of turns sufficient to provide fixation, such as 0.5 to 2 turns. Fewer turns mitigates risk of puncturing through the septum. The following materials may be utilized for the helix 634 wire: Pt 80%/Ir 20% or Pt 90%/Ir 10% for a thinner wire.

FIGS. 13A-13F illustrate example blunt wire ends suitable for use as a blunt helix, such as helix 34, 134, 334, 434, 534, and, optionally, 634. For simplicity the helical shape of the wire is not shown. The examples of FIGS. 13A-13F are not limiting as other shapes and textures may be used as blunt wire ends suitable for use as a blunt helix.

Figure 13A:
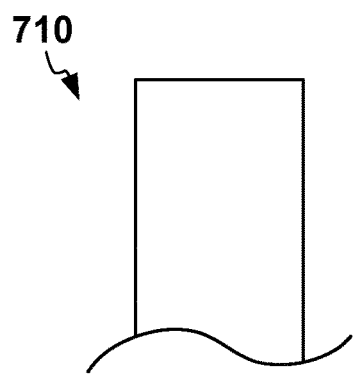
FIGS. 13A-13F illustrate example blunt wire ends suitable for use as a blunt helix.

FIG. 13A illustrates blunt wire tip 710. Wire tip 710 has a flat surface about perpendicular to the diameter of the wire. The surface of blunt wire tip 710 is dull such that a thickness of the blunt wire tip 710 is at least one-half of the width of the wire as measured proximal to a distal tip at an offset equal to the width of the helix wire, such as at least 75 percent of the width of the helix wire as measured proximal to the distal tip at the offset equal to the width of the helix wire.

Figure 13B:
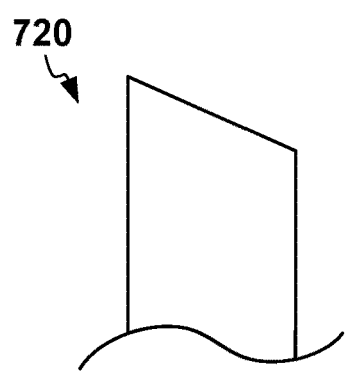

FIG. 13B illustrates blunt wire tip 720. Wire tip 720 has a flat surface at a nonperpendicular angle to the diameter of the wire. However, the angle is such that a thickness of the blunt wire tip 720 is at least one-half of the width of the wire as measured proximal to a distal tip at an offset equal to the width of the helix wire, such as at least 75 percent of the width of the helix wire as measured proximal to the distal tip at the offset equal to the width of the helix wire.

Figure 13C:
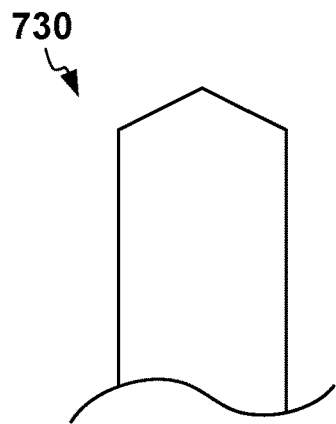

FIG. 13C illustrates blunt wire tip 730. Wire tip 730 has a beveled surface at two complimentary angles. However, in contrast to a standard sharp helix, the beveled angles are such that a thickness of the blunt wire tip 730 is at least one-half of the width of the wire as measured proximal to a distal tip at an offset equal to the width of the helix wire, such as at least 75 percent of the width of the helix wire as measured proximal to the distal tip at the offset equal to the width of the helix wire.

Figure 13D:
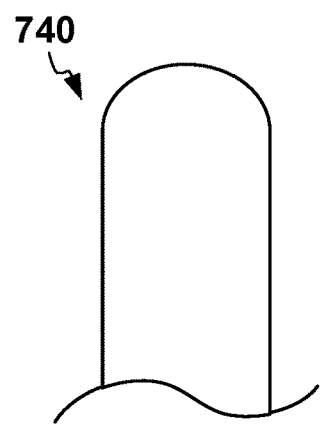

FIG. 13D illustrates blunt wire tip 740. Wire tip 740 has a rounded surface. The rounded surface is dull such that a thickness of the blunt wire tip 740 is at least one-half of the width of the wire as measured proximal to a distal tip at an offset equal to the width of the helix wire, such as at least 75 percent of the width of the helix wire as measured proximal to the distal tip at the offset equal to the width of the helix wire.

Figure 13E:
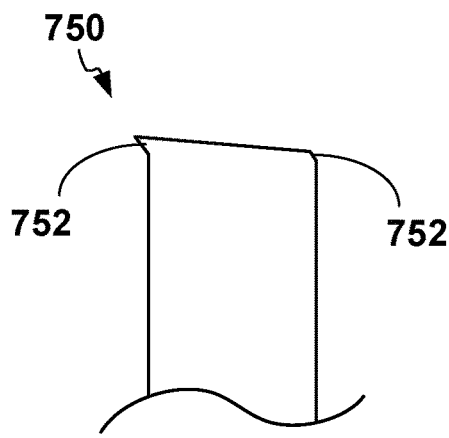
Figure 13F:
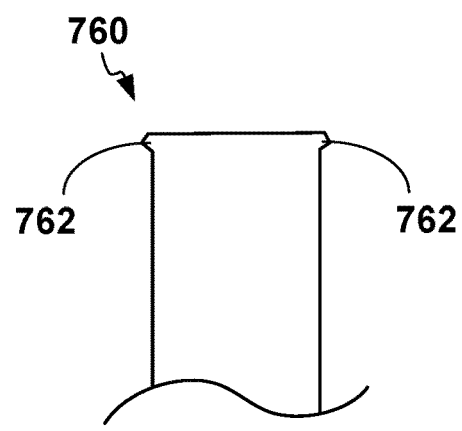

FIG. 13E illustrates blunt wire tip 750. Wire tip 750 has a generally flat surface, but includes a protruding deformity 752 that protrudes beyond a nominal cross-section of the wire, and a rounded deformity with material missing from the nominal cross-section of the wire. The deformities 752, 754 may be the result of a cutting operation used to form blunt wire tip 750. The surface of blunt wire tip 750 is dull such that a thickness of the blunt wire tip 750 is at least one-half of the width of the wire as measured proximal to a distal tip at an offset equal to the width of the helix wire, such as at least 75 percent of the width of the helix wire as measured proximal to the distal tip at the offset equal to the width of the helix wire.

FIG. 13E illustrates blunt wire tip 760. Wire tip 760 has a generally flat surface, but includes a protruding deformity 762 that protrudes beyond a nominal cross-section of the wire on both sides of the wire and potentially all around the perimeter of the wire end. The deformity 762 may be the result of a grinding or sanding operation used to form blunt wire tip 760. The surface of blunt wire tip 760 is dull such that a thickness of the blunt wire tip 760 is at least one-half of the width of the wire as measured proximal to a distal tip at an offset equal to the width of the helix wire, such as at least 75 percent of the width of the helix wire as measured proximal to the distal tip at the offset equal to the width of the helix wire.

A number of modifications to the techniques described herein are within the spirit of this disclosure. For example, while the disclosed techniques are described with respect to selecting the trajectory of an electrode for His bundle pacing, LBB pacing and/or RBB pacing, the leads and other techniques disclosed herein may also be used for different target sites, for cardiac pacing and otherwise.

As another example, the disclosed techniques could be used with any pulse generator, whether it is in the pectoral pocket, abdomen, or in the right ventricle. In this manner, the transseptal pacing leads disclosed herein are suitable with any implantable pulse generator using any particular pacing programming therapies and/or cardiac sensing techniques.

Various examples of this disclosure have been described. These and other examples are within the scope of the following claims.

The invention claimed is:

1. A medical lead comprising:
   a lead body;
   a lead body helix extending from a distal end of the lead body, wherein the lead body helix is configured to anchor to a patient tissue;
   a lead body electrode proximate a distal end of the lead body;
   a lead body conductor electrically connected to the lead body electrode and extending from lead body electrode to a proximal portion of the lead body; and
   a cable within the lead body, the cable including a cable conductor, a cable electrode proximate a distal end of the cable conductor, and a cable helix with a blunt tip at a distal end of the cable,
   wherein a coil diameter of the cable helix is within a range of 1 French (0.013 inches) to 3 French (0.039 inches), and
   wherein the cable is slidable within the lead body to extend and retract the cable electrode along a trajectory extending from the distal end of the lead body.

2. The medical lead of claim 1,
   wherein the cable helix is formed from a wire, and
   wherein the blunt tip includes a rounded or flat frontal surface extending across a width of the wire.

3. The medical lead of claim 2, wherein a thickness of the blunt tip is at least one-half of the width of the wire as measured proximal to a distal tip at an offset equal to the width of the wire.

4. The medical lead of claim 3, wherein the thickness of the blunt tip is at least 75 percent of the width of the wire as measured proximal to the distal tip at the offset equal to the width of the wire.

5. The medical lead of claim 1, wherein the cable helix is encased in a coating of mannitol, the mannitol forming the blunt tip at the distal end of the cable.

6. The medical lead of claim 1, wherein the lead body helix has a sharpened tip.

7. The medical lead of claim 6, wherein the lead body helix is formed from a wire, wherein the sharpened tip is a beveled angle tip in the wire.

8. The medical lead of claim 1, wherein when the lead body helix is anchored to the patient tissue, the cable helix is configured to blunt dissect the patient tissue along the trajectory extending from the distal end of the lead body through extension of the cable.

9. The medical lead of claim 1, wherein the cable is slidable within the lead body to extend the cable electrode at least 1.8 centimeters from the distal end of the lead body.

10. The medical lead of claim 1, wherein the cable helix has 0.5 to 2 turns.

11. The medical lead of claim 1, wherein a coil diameter of the cable helix is within a range of 1.5 French (0.020 inches) to 2.5 French (0.033 inches).

12. The medical lead of claim 1, wherein the cable helix forms the cable electrode.

13. The medical lead of claim 1, wherein the lead body electrode includes a helical electrode formed by the helix.

14. The medical lead of claim 1, wherein the lead body electrode includes a ring electrode proximate to the distal end of the lead body.

15. The medical lead of claim 1, further comprising a connector proximate to a proximal end of the lead body, wherein the lead body conductor electrically connects the lead body electrode to the connector.

16. The medical lead of claim 15, wherein the connector includes a connector pin and a ring terminal, wherein the lead body conductor electrically connects the ring terminal to the lead body helix.

17. The medical lead of claim 15, wherein the lead body conductor connects the lead body helix to a first electrode of the connector,
   wherein the cable conductor connects the cable electrode to a second electrode of the connector.

18. The medical lead of claim 17, wherein the second electrode is a connector pin.

19. The medical lead of claim 1, wherein the cable conductor includes a conductor selected from a group consisting of:
   a coil conductor;
   a solid wire; and
   a stranded wire.

20. The medical lead of claim 1, wherein the cable conductor is an insulated cable conductor.

21. A method for implanting a medical lead of claim 1, the method comprising:
   securing the lead body helix of to a patient tissue proximate a target site;
   extending the cable conductor from the lead body to blunt dissect the patient tissue with the cable helix; and
   rotating the cable conductor relative to the lead body to anchor the cable helix to the patient tissue.

22. The method of claim 21, wherein extending the cable conductor from the lead body extends the cable electrode at least 1.8 centimeters from the distal end of the lead body.

23. The method of claim 21, wherein securing the lead body helix of the medical lead to the patient tissue includes:
   positioning a distal end of a catheter proximate the target site;

delivering a distal end of the medical lead proximate the target site via the catheter; and rotating the lead body helix to anchor the lead body helix to the patient tissue.

24. The method of claim 23, further comprising, after securing the lead body helix, manipulating the catheter to set the trajectory for deploying the cable electrode within the patient tissue, wherein manipulating the catheter includes one or more of:

bending the catheter through pushing and pulling from a proximal location outside the body of the patient; and rotating the catheter.

25. The method of claim 21, wherein the target site is a septum of the patient.

26. The method of claim 21, wherein deploying the cable electrode within the patient tissue comprises deploying the cable electrode within the patient tissue to contact a left bundle branch of the patient.

27. The method of claim 21, wherein the target site is a septum of the patient, wherein, with the lead body helix is anchored to the patient tissue and the cable electrode deployed within the patient tissue, the cable electrode is proximal to a left bundle branch and a right bundle branch of the patient, and wherein, with the lead body helix is anchored to the patient tissue and the cable electrode deployed within the patient tissue, the lead body electrode is proximal to the right bundle branch.

28. The method of claim 27, wherein the lead body helix forms the lead body electrode, and wherein the cable helix forms the cable electrode.

29. The medical lead of claim 1, wherein the lead body electrode is attached to the lead body proximate to the distal end of the lead body.

* * * * *